(12) United States Patent
McCabe Dunn et al.

(10) Patent No.: US 11,634,511 B2
(45) Date of Patent: Apr. 25, 2023

(54) PROCESSES FOR THE PREPARATION OF SUGAMMADEX

(71) Applicants: Merck Sharp & Dohme Corp., Rahway, NJ (US); Jamie M. McCabe Dunn, Cranford, NJ (US); Nadine Kuhl, Garwood, NJ (US); Wenyong Chen, Princeton, NJ (US); Yang Cao, Scotch Plains, NJ (US); Donald R. Gauthier, Jr., Westfield, NJ (US); Alan Michael Hyde, Metuchen, NJ (US); Susan L. Zultanski, Brooklyn, NY (US)

(72) Inventors: Jamie M. McCabe Dunn, Cranford, NJ (US); Nadine Kuhl, Garwood, NJ (US); Wenyong Chen, Princeton, NJ (US); Yang Cao, Scotch Plains, NJ (US); Donald R. Gauthier, Jr., Westfield, NJ (US); Alan Michael Hyde, Metuchen, NJ (US); Susan L. Zultanski, Brooklyn, NY (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 0 days.

(21) Appl. No.: 17/059,925

(22) PCT Filed: Jun. 3, 2019

(86) PCT No.: PCT/US2019/035104
§ 371 (c)(1),
(2) Date: Nov. 30, 2020

(87) PCT Pub. No.: WO2019/236436
PCT Pub. Date: Dec. 12, 2019

(65) Prior Publication Data
US 2021/0206884 A1   Jul. 8, 2021

Related U.S. Application Data

(60) Provisional application No. 62/681,889, filed on Jun. 7, 2018.

(51) Int. Cl.
*C08B 37/16*        (2006.01)
(52) U.S. Cl.
CPC ................ *C08B 37/0012* (2013.01)
(58) Field of Classification Search
CPC .................................................. C08B 37/0012
See application file for complete search history.

(56) References Cited

U.S. PATENT DOCUMENTS

| 2011/0045101 | A1 | 2/2011 | Selby et al. |
| 2012/0264734 | A1 | 10/2012 | Kuntz et al. |
| 2014/0221641 | A1 | 8/2014 | Davuluri et al. |
| 2016/0009827 | A1 | 1/2016 | Ravi et al. |
| 2018/0016359 | A1 | 1/2018 | Jia et al. |
| 2018/0171033 | A1* | 6/2018 | Alaparthi ............... A61P 39/02 |
| 2018/0208683 | A1* | 7/2018 | Lee ..................... C08B 37/0012 |

FOREIGN PATENT DOCUMENTS

| WO | 2001040316 | A1 | 6/2001 | |
| WO | WO-2017089966 | A1 * | 6/2017 | ......... C08B 37/0003 |
| WO | 2017144734 | A2 | 8/2017 | |
| WO | 2017163165 | A1 | 9/2017 | |

OTHER PUBLICATIONS

Kurochkina, G. et al "Synthesis of oligo-6-bromo-6-deoxy-b-cyclodextrins" Russ. J. Gen. Chem., vol. 74, No. 10, pp. 1620-1622. (Year: 2004).*
Hodosi et al "The mechanism of the hydroxyl -> exchange . . . " Carbohyd. Res., vol. 230, pp. 327-342. (Year: 1992).*
Mitchell, J. "Kark Fischer reagent titration" Anal. Chem. vol. 23, No. 8, pp. 1069-1075. (Year: 1951).*
Adam, J.M. et al., Cyclodextrin-Derived Host Molecules as Reversal Agents for the Neuromuscular Blocker Rocuronium Bromide: Synthesis and Structure-Activity Relationships, J. Med. Chem., 2002, 1806-1816, 45.
Chmurski, K. et al., An Improved Synthesis of 6-Deoxyhalo Cyclodextrins via Halomethylenemorpholinium Halides Vilsmeier-Haack Type Reagents, Tetrahedron Letters, 1997, 7365-7368, 38.
Gorin, Boris I. et al., Efficient Perfacial Derivatization of Cyclodextrins at the Primary Face, Tetrahedron Letters, 1996, 4647-4650, 37(27).
Larsson, W. et al., Efficiency of Methods for Karl Fischer Determination of Water in Oils Based on Oven Evaporation and Azeotropic Distillation, Analytical Chemistry, 2003, 1227-1232, 75.
Murakami, S. et al., Effects of salt or cosolvent addition on solubility of a hydrophobic solute in water: Relevance to those on thermal stability of a protein, The Journal of Chemical Physics, 2017, 1-15, 146.
Baer, Hans H. et al., Improved preparation of hexakis(6-deoxy)cyclomalto-hexaose and heptakis(6-deoxy) cyclomaltoheptaose, Carbohydrate Research, 1992, 307-314, 228.
Chmurski, K. et al., Regioselective Halogenation of Primary Alcohol Groups of Cyclodextrins with Halomethylenemorpholinium Halides Vilsmeier-Haack Reagents, Polish J. Chem., 1999, 967-971, 73.
Chmurski, Kazimierz et al., An Improved Synthesis of Per(6-Deoxyhalo) Cyclodextrins Using N-Halosuccinimides-Triphenylphosphine in Dimethylformamide, Supramolecular Chemistry, 2000, 221-224, 12:2.
Gadelle, Andree et al., Selective Halogenation at Primary Positions of Cyclomaltooligosaccharides and a Synthesis of Per-3,6-anhydro Cyclomaltooligosaccharides, Angew. Chem. Int. Ed. Engl., 1991, 78-80, 30.

(Continued)

*Primary Examiner* — Leigh C Maier
(74) *Attorney, Agent, or Firm* — Sylvia A. Ayler; Catherine D. Fitch

(57) ABSTRACT

The present invention provides processes for the preparation of sugammadex: (I) In one aspect, there is provided a process for the preparation of sugammadex from 8-per-deoxy-8-bromo-γ-cyclodextrin and 3-mercaptopropionic acid. In another aspect, there is provided an alternative process for the preparation of sugammadex from 8-per-deoxy-8-bromo-γ-cyclodextrin and disodium 3-mercaptopropionate. In another aspect, there is provided a process for the preparation of 8-per-deoxy-8-bromo-γ-cyclod extrin, which may be used in the production of sugammadex. In one such aspect, there is provided a process for the preparation (Continued)

of 8-per-deoxy-8-bromo-γ-cyclodextrin from γ-cyclodextrin and a brominating agent. In another such aspect, there is provided a process for the preparation of 8-per-deoxy-8-bromo-γ-cyclodextrin comprising, inter alia, reacting γ-cyclodextrin with an electrophilic brominating agent, a deoxygenating agent, and an acid in the presence of an organic solvent.

(I)

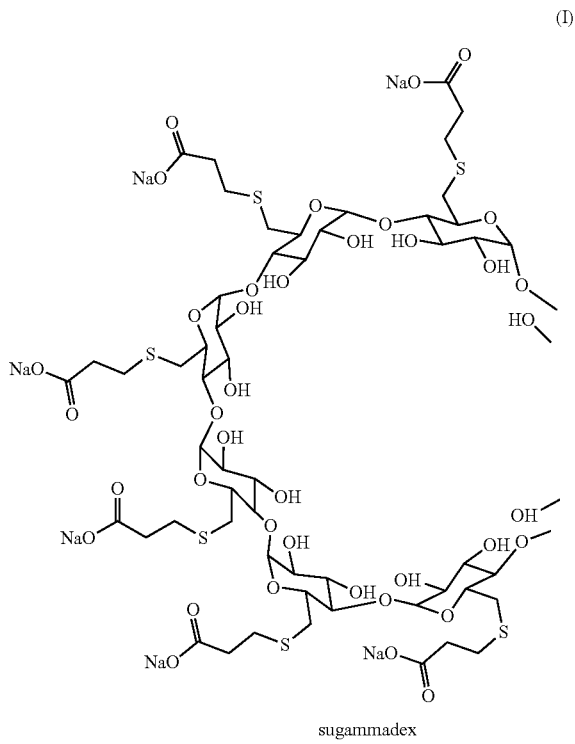

sugammadex

-continued

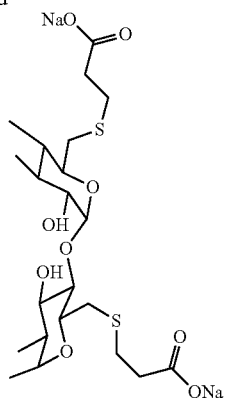

21 Claims, No Drawings

(56) References Cited

OTHER PUBLICATIONS

Khan, Abdul Rauf et al., Synthesis of 6-Deoxychlorocyclodextrin via Vilsmeier-Haack-Type Complexes, J. Org. Chem., 1994, 7492-7495, 59.
Takeo, K. et al., An Improved Synthesis of 6-Deoxy-Analogues of Cyclodextrins and Amylose, Stärke, 1974, 111-118, 26.
Yang, Qiang et al., Potential Explosion Hazards Associated with the Autocatalytic Thermal Decomposition of Dimethyl Sulfoxide and Its Mixtures, Org. Process Res. Dev., 2020, 916-939, 24.

* cited by examiner

PROCESSES FOR THE PREPARATION OF SUGAMMADEX

CROSS REFERENCE TO RELATED APPLICATIONS

This application is a U.S. National Phase application under 35 U.S.C. § 371 of PCT Application No. PCT/US2019/035104 filed Jun. 3, 2019, which claims priority from U.S. Ser. No. 62/681,889 filed Jun. 7, 2018.

FIELD OF THE INVENTION

This invention relates to a novel process for making the pharmaceutical product sugammadex.

BACKGROUND

Sugammadex is a modified cyclodextrin having the following structure:

Sugammadex was approved in 2008 by the EMEA and in 2015 by the USFDA for the reversal of neuromuscular blockade induced by rocuronium bromide and vecuronium bromide in adults undergoing surgery. It is marketed in the form of a sterile solution for intravenous injection under the brand name BRIDION®. Sugammadex is disclosed and claimed in WO2001/040316, published Jun. 7, 2001, together with a method for its synthesis. There remains a need in the art for an improved synthesis of sugammadex. The present invention addresses this need.

SUMMARY OF THE INVENTION

The present invention provides processes for the preparation of sugammadex. In one aspect, there is provided a process for the preparation of sugammadex:

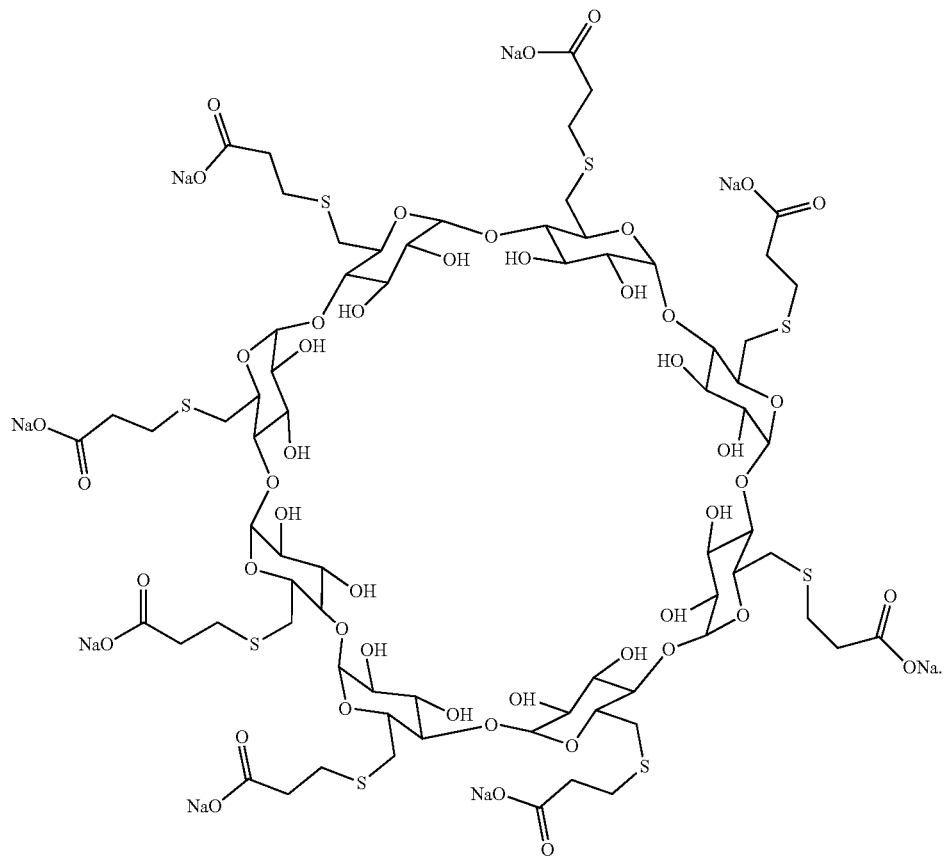

sugammadex

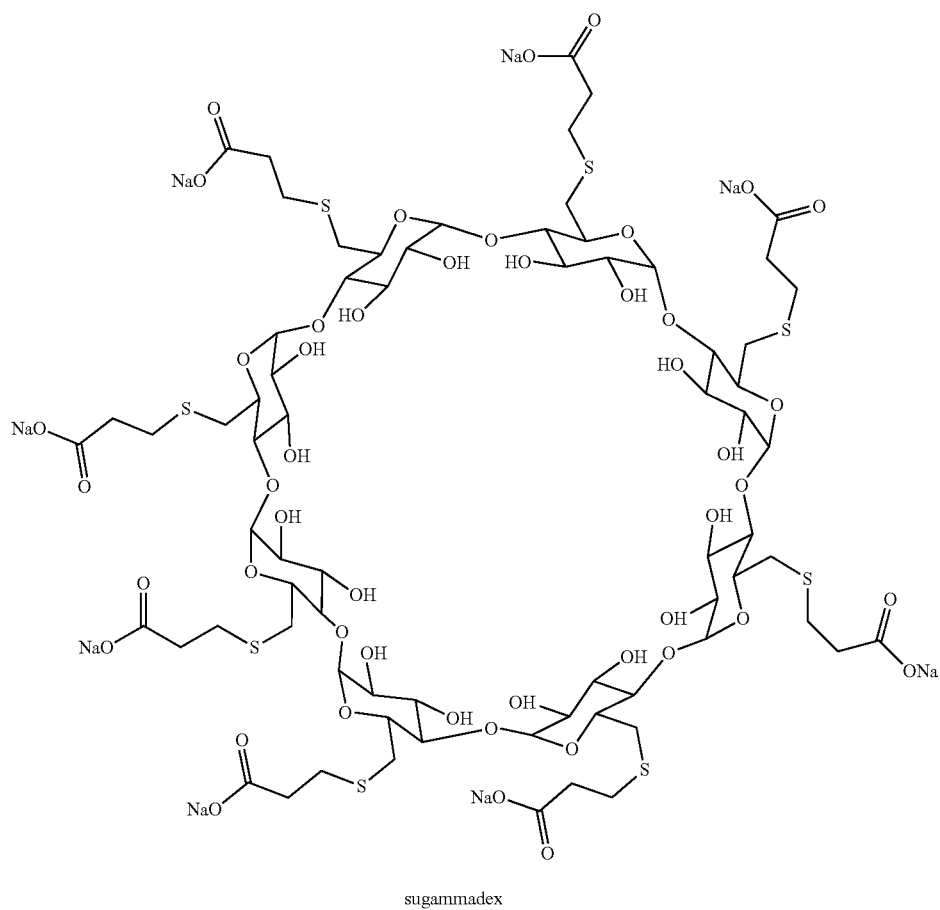

sugammadex comprising:

dissolving 8-per-deoxy-8-bromo-γ-cyclodextrin in a solvent;

adding 3-mercaptopropionic acid to form a first solution;

adding a base-water solution to the first solution at a rate sufficient to maintain the temperature of the resulting solution between about 5° C. and 40° C.;

stirring the resulting solution in the presence of heat;

adjusting the pH of the resulting mixture to from 7 to 13; and isolating the sugammadex product.

In another aspect, there is provided a process for the preparation of sugammadex

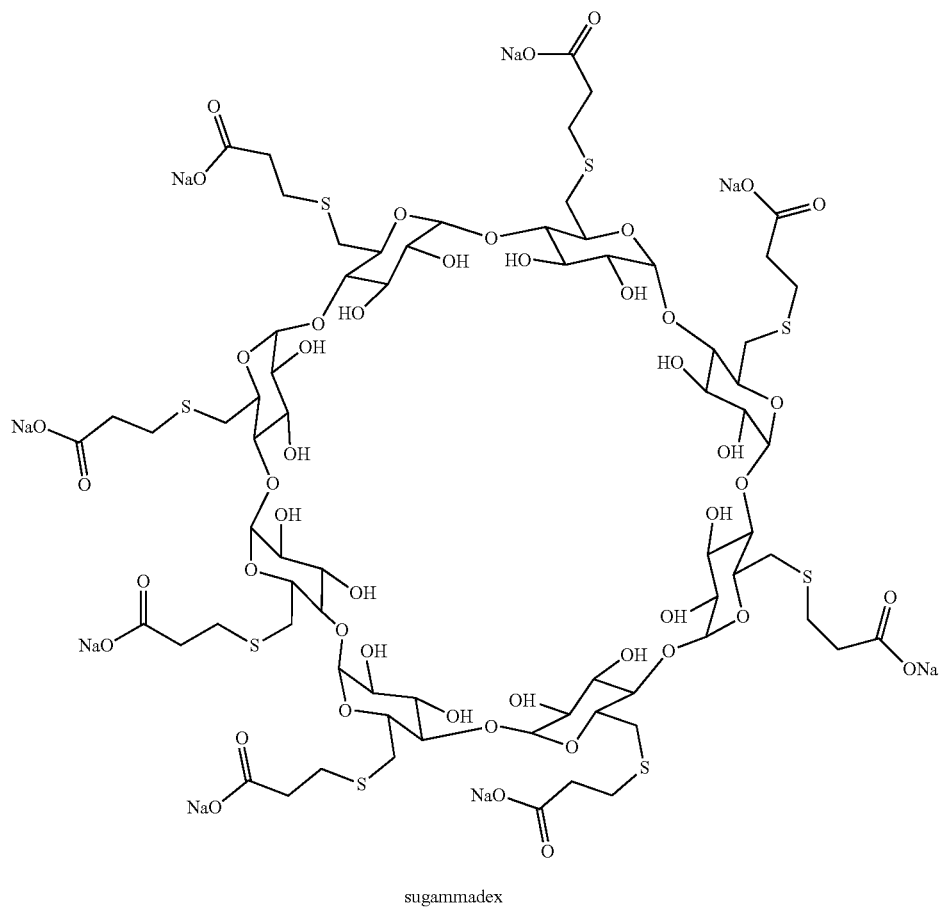

sugammadex comprising:
dissolving a solubility enhancing reagent in a solvent mixture to form a first solution;
adding disodium 3-mercaptopropionate to the first solution to form a second solution;
adding 8-per-deoxy-8-bromo-γ-cyclodextrin to the second solution to form a third solution;
stirring the third solution in the presence of heat; and
isolating the sugammadex product.

In another aspect, there is provided a process for the preparation of 8-per-deoxy-8-bromo-γ-cyclodextrin of the formula:

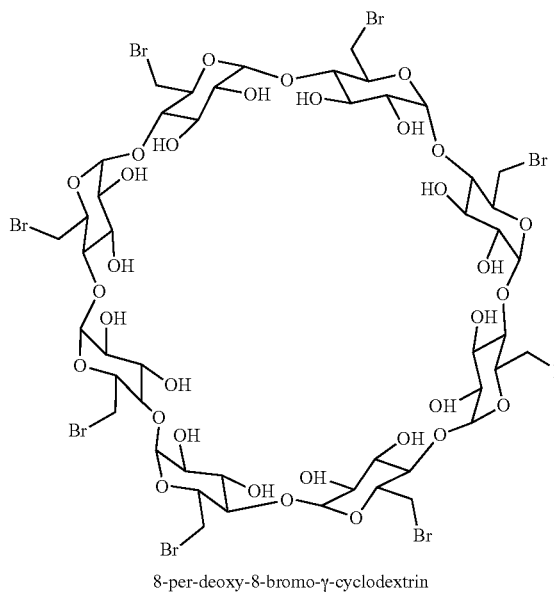

8-per-deoxy-8-bromo-γ-cyclodextrin

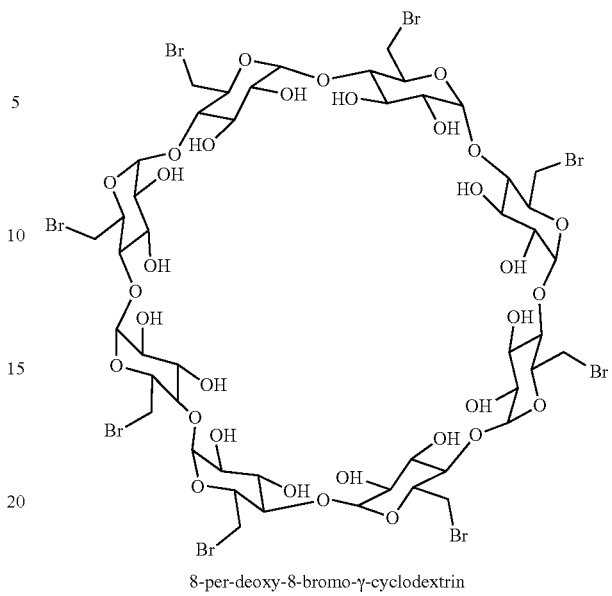

8-per-deoxy-8-bromo-γ-cyclodextrin comprising:

forming a solution comprising γ-cyclodextrin of the formula:

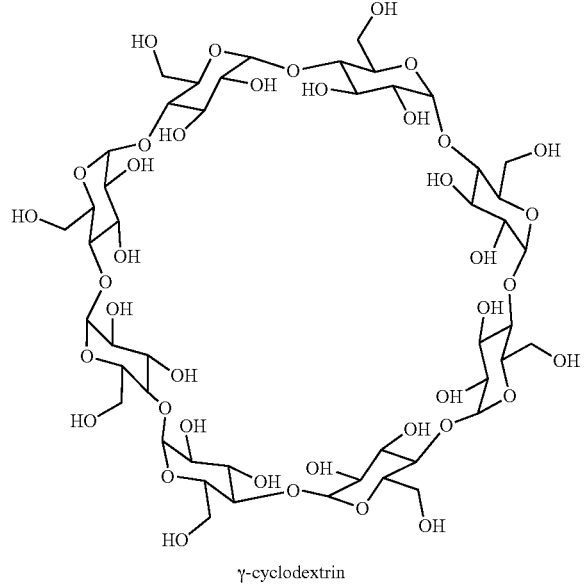

γ-cyclodextrin an organic solvent; and a brominating agent;

heating the resulting solution; and isolating the 8-per-deoxy-8-bromo-γ-cyclodextrin. The product 8-per-deoxy-8-bromo-γ-cyclodextrin from γ-cyclodextrin may be used as starting material in either of the above aspects of the invention for the production of sugammadex. In a preferred embodiment, an amount of water sufficient to quench the reaction is added to the resulting solution prior to isolation.

In another aspect, there is provided an alternative process for the preparation of 8-per-deoxy-8-bromo-γ-cyclodextrin of the formula:

comprising:

reacting γ-cyclodextrin of the formula:

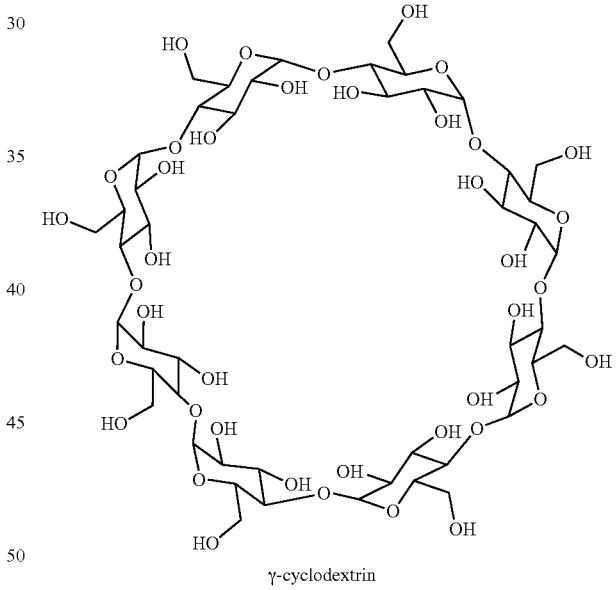

γ-cyclodextrin with an electrophilic brominating agent, a deoxygenating agent, and an acid in the presence of an organic solvent;

heating the resulting mixture;

adding to the mixture a solution comprising water and an acid and mixing the resulting solution; and isolating the 8-per-deoxy-8-bromo-γ-cyclodextrin. The product 8-per-deoxy-8-bromo-γ-cyclodextrin from γ-cyclodextrin may be used as starting material in either of the above aspects of the invention in the production of sugammadex.

The examples provided herein are for illustrative purposes so that the invention may be more fully understood. These examples should not be construed as limiting the invention in any way.

DETAILED DESCRIPTION OF THE INVENTION

Abbreviations r.t. (or R.T.): Room Temperature
DEF: N,N-diethylformamide
DMF: N,N-dimethylformamide
DMA: N,N-dimethylacetamide
DMI: 1,3-dimethyl-2-imidazolidinone
DMPU: 1,3-dimethyl-3,4,5,6-tetrahydro-2(1H)-pyrimidinone
DMSO: dimethylsulfoxide
DME: 1,2-dimethoxyethane
H (or h): hour(s)
HPLC: high pressure liquid chromatography
KF: Karl Fischer titration
NMP: 1-methyl-2-pyrrolidinone
Py: Pyridine
TMU: 1,1,3,3-tetramethylurea
TEG: triethylene glycol
V: volume(s) is defined as the amount of solvent used based on the amount of the relevant limiting reagent; i.e., 1V (or 1v)=1 ml solvent for each gram of the limiting reagent.

Solvents and reagents that are commercially available were used as received. All solvents and reagents indicated as being commercially available may be obtained from many commercial suppliers, including, e.g., Sigma Aldrich, St. Louis, Mo., USA.

PREPARATION OF SUGAMMADEX FROM 8-PER-DEOXY-8-BROMO-GAMMA-CYCLODEXTRIN AND 3-MERCAPTOPROPIONIC ACID

In one aspect, there is provided a process for the preparation of sugammadex:

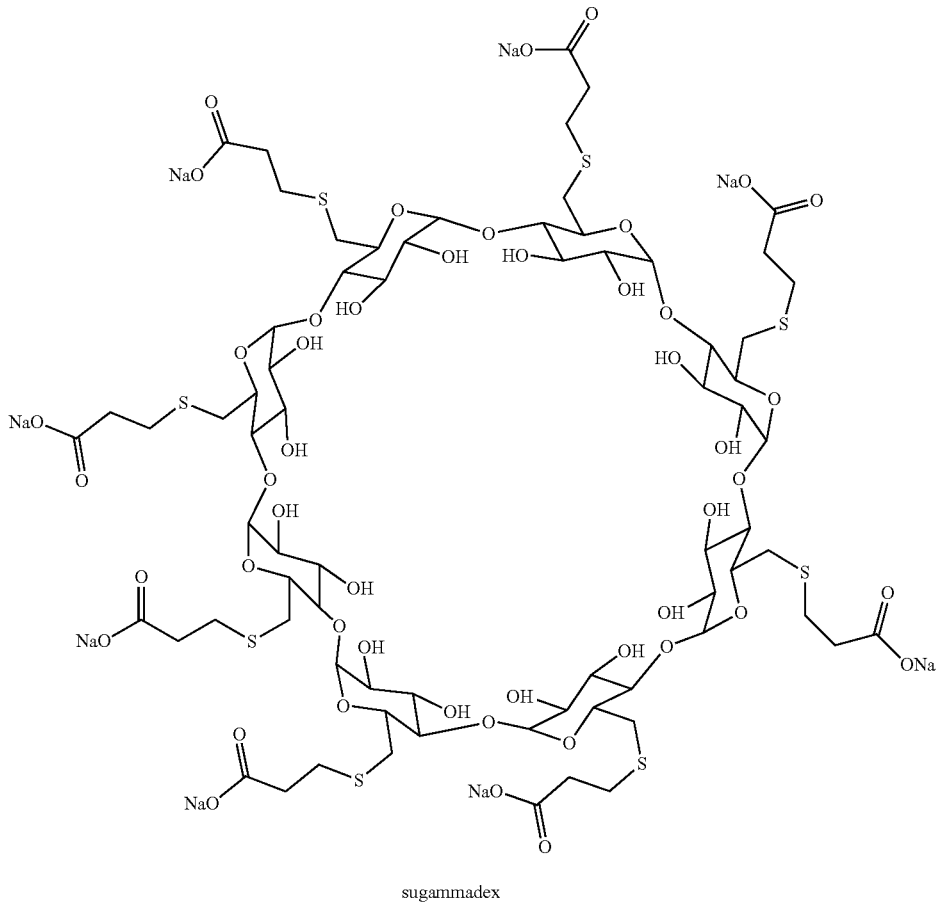

sugammadex comprising:
dissolving 8-per-deoxy-8-bromo-γ-cyclodextrin in a solvent;
adding 3-mercaptopropionic acid to form a first solution;
adding a base-water solution to the first solution at a rate sufficient to maintain the temperature of the resulting solution between about 5° C. and 40° C.;
stirring the resulting solution in the presence of heat;
adjusting the pH of the resulting mixture to from 7 to 13; and
isolating the sugammadex product.

Expediently, the base-water solution and the first solution may be prepared in separate reactors (or other suitable containers or vessels) before they are combined. Suitable reactors, containers or vessels are well known to those of ordinary skill in the art.

As noted above, 8-per-deoxy-8-bromo-γ-cyclodextrin is dissolved in a solvent and 3-mercaptopropionic acid is added to form a first solution. Suitable solvents useful for forming the first solution are available commercially. In one embodiment, the solvent is an organic solvent. In another embodiment, the solvent is 1-methyl-2-pyrrolidinone (NMP), N,N-dimethylformamide (DMF); N,N-diethylformamide (DEF); 1,3-dimethyl-2-imidazolidinone (DMI); 1,3-dimethyl-3,4,5,6-tetrahydro-2(1H)-pyrimidinone (DMPU); pyridine (Py); 1,2-dimethoxyethane (DME); 1,1,3,3-tetramethylurea (TMU); triethylene glycol (TEG); dimethylsulfoxide (DMSO); water; diethyl carbonate; methanol; N,N-dibutylformamide; N,N-dimethylacetamide (DMA); N,N-diethylacetamide; 1-ethyl-2-pyrrolidone; 1-octyl-2-pyrrolidone; or 1-cyclohexyl-2-pyrrolidone; or mixture thereof In a preferred embodiment, the solvent is 1-methyl-2-pyrrolidinone (NMP).

In one embodiment, the temperature of the first solution comprising the 8-per-deoxy-8-bromo-γ-cyclodextrin, solvent, and 3-mercaptopropionic acid is controlled during the addition of the base-water solution. In one embodiment, the temperature of the first solution is maintained (or adjusted to be) in the range of 18° C. to 35° C. In another such embodiment, the temperature of the first solution is maintained in the range of 25° C. to 32° C. In another such embodiment, the temperature of the first solution is maintained in the range of 5° C. to 40° C. In another such embodiment, the temperature of the first solution is maintained in the range of 10° C. to 30° C. In another such embodiment, the temperature of the first solution is maintained in the range of 15° C. to 25° C. In another such embodiment, the temperature of the first solution is maintained at 20° C.

A base-water solution suitable for use in the present invention may be purchased or prepared by methods known to those of skill in the art. In one non-limiting embodiment, the base-water solution may be prepared by mixing a suitable base and water. Suitable bases for use in the base-water solution are available commercially. In one embodiment, the base is sodium hydroxide, sodium carbonate, sodium phosphate, sodium bis(trimethylsilyl)amide, sodium tert-butoxide, or sodium tert-pentoxide, or mixtures thereof. In a preferred embodiment, the base is sodium hydroxide. In an alternative of each of the preceding embodiments, the concentration of base in water ranges from 6% to 24%. In another alternative of each of the preceding embodiments, the concentration of base in water ranges from 10% to 15%. In an alternative of each of the preceding embodiments, the concentration of base in water ranges from 13% to 14%.

In one embodiment, the base-water solution according to any of the embodiments described above is added slowly to the first solution. In one such embodiment, the base-water solution according to any of the embodiments described above is added over at least one hour or more.

After the base-water solution according to any of the embodiments described above is added to the first solution is completed, the resulting solution is stirred in the presence of heat. In one embodiment, after the addition of the base-water solution to the first solution is completed, the resulting solution is heated to a temperature of at least 20° C. In another embodiment, the solution is heated to a temperature between 20° C. and 100° C. In another embodiment, the solution is heated to a temperature between 40° C. and 70° C. In another embodiment, the solution is heated to a temperature between 40° C. and 60° C. In another embodiment, the solution is heated to a temperature between 45° C. and 65° C. In one embodiment, the solution is heated to a temperature of about 50° C. In one embodiment, the solution is stirred for at least 1 hour (in another embodiment at least 2 hours) while the temperature is maintained according to any of the embodiments described in the paragraph above. In another embodiment, the solution is stirred for from 1 hour to 30 hours (in another embodiment for from 2 hours to 30 hours) while the temperature is maintained according to any of the embodiments described in the paragraph above. In another embodiment, the solution is stirred for about 10 hours at about 50° C. In another embodiment, the solution is stirred for about 4 hours at about 50° C.

The pH of the resulting solution is then adjusted to from 6 to 13 by the addition of a suitable amount of acid or base as needed. In one embodiment, the pH of the resulting solution is adjusted to from 6.7 to 13. In another embodiment, the pH of the resulting solution is adjusted to from 7 to 13. In one embodiment, the pH of the resulting solution is adjusted to from 7 to 9.5. In another embodiment, the pH of the resulting solution is adjusted to from 7 to 10. In another embodiment, the pH of the resulting solution is adjusted to from 7.5 to 8. In another embodiment, the pH of the resulting solution is adjusted to from 8.5 to 9.5. Suitable acids and bases are commercially available and known to those of ordinary skill. In one embodiment, the acid is selected from hydrochloric acid, sulfuric acid, phosphoric acid, hydrobromic acid, acetic acid, methanesulfonic acid, p-toluenesulfonic acid, trifluoroacetic acid, trifluoromethanesulfonic acid. (all acids are available at Sigma Aldrich) and mixtures thereof; the base (if needed) is sodium hydroxide, sodium carbonate, sodium phosphate, sodium bicarbonate, sodium hydrogenphosphate, sodium ethoxide, or sodium methoxide (all bases are available at Sigma Aldrich), and mixtures thereof. In one embodiment, the acid is aqueous hydrochloric acid and the base (if needed) is sodium hydroxide.

The thus produced sugammadex is optionally isolated. In one embodiment, isolation is achieved by adding an antisolvent to the solution to precipitate sugammadex. Suitable antisolvents are commercially available. In one embodiment, the antisolvent is methanol, ethanol, isopropanol or tetrahydrofuran. In a preferred embodiment, the antisolvent is methanol.

Preferably the antisolvent is added slowly. In one embodiment, the antisolvent, which may be selected from any of the embodiments described above, is added over at least 20 minutes.

After the addition of antisolvent has been completed, the resulting solution is optionally stirred to form a slurry. In one embodiment, the solution is stirred for at least 30 minutes. In another embodiment, the solution is stirred for from 30 minutes to 24 h. In a preferred embodiment, the solution is stirred for 2 hours after the addition of the antisolvent.

The slurry formed is filtered, and the collected solid is washed with solvent or a mixture of water and solvent. Suitable solvents are available commercially and include, but are not limited to methanol, ethanol, isopropanol, NMP, and mixtures thereof, and mixtures of such solvents and water. The obtained solid may be dried, e.g., under vacuum, to yield the desired product.

Example 1: Preparation of sugammadex from 8-per-deoxy-8-bromo-γ-cyclodextrin and 3-Mercaptopropionic Acid

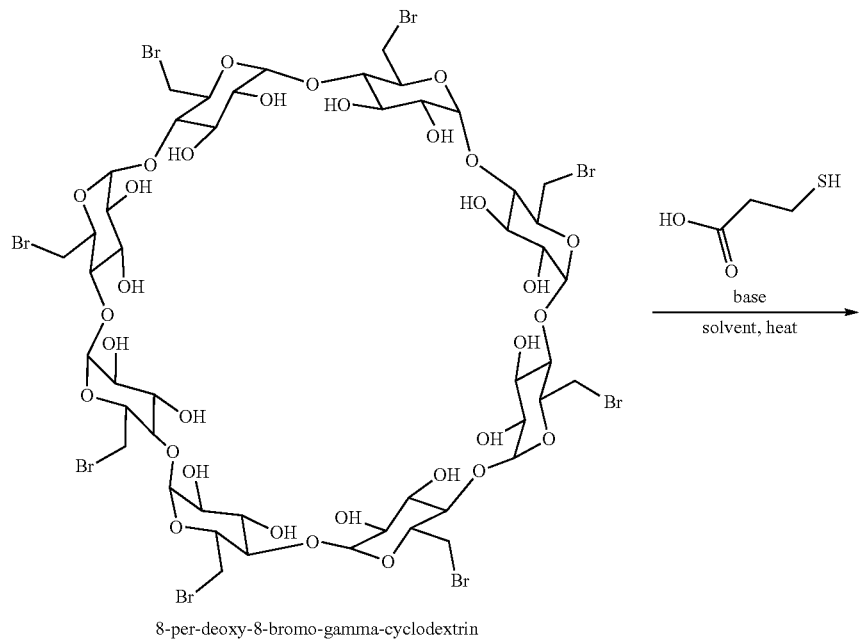

8-per-deoxy-8-bromo-gamma-cyclodextrin

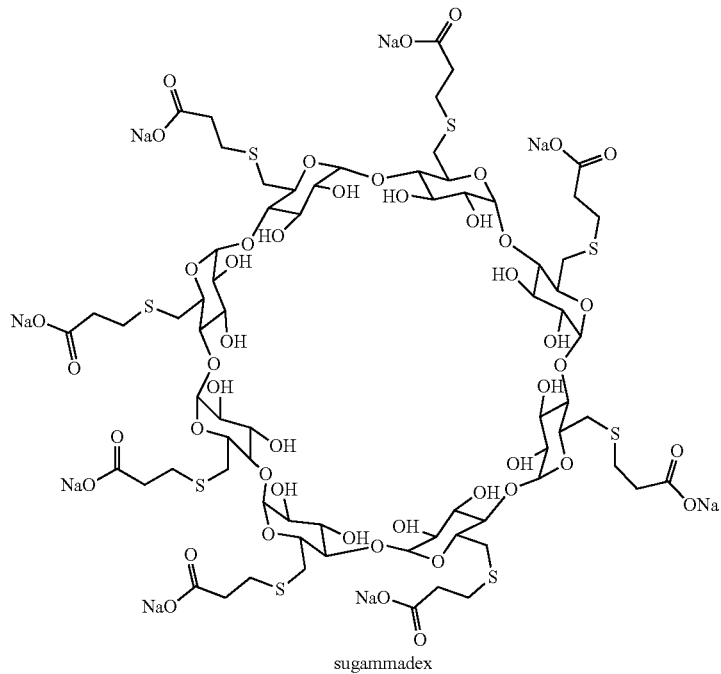

sugammadex

In a 10 L reactor, 8-per-deoxy-8-bromo-γ-cyclodextrin (400.0 g, 196.64 mmol, 88.5 wt%) was dissolved in NMP (2000 mL) and 3-mercaptopropionic acid (273.6 mL, 3144 mmol) was added. The solution was cooled to 20° C. The sodium hydroxide-water solution (1600 mL, 6080 mmol, 13.4 wt%) was added to the solution in the 10L reactor over 1.5 h while maintaining the temperature between 20-23° C. After the addition was complete, the reaction was heated to 50° C. and stirred for 3 h. The desired product was isolated. Isolation was achieved by adjusting the pH to 7-8 using 6 N aqueous HCl (231.2 mL, 1141.4 mmol). Methanol (2800 mL) was then added at 18° C. to 20° C. over 2 hours and the mixture was stirred for 2 hours at 18° C. to 20° C. The slurry was filtered, and the solid was washed with 8:1 methanol: water (v/v) (2000 mL). The obtained solid was dried under vacuum to yield the desired sugammadex product in 449.2 g (87.74 wt%, 92% isolated yield). The analytical data characterizing the obtained sugammadex was in agreement with characterizations of the same provided in the literature. Adam, J. M., et al. J. Med. Chem. 2002, 45, 1806-1816.

Example 1A: Preparation of sugammadex from 8-per-deoxy-8-bromo-γ-cyclodextrin and 3-Mercaptopropionic Acid

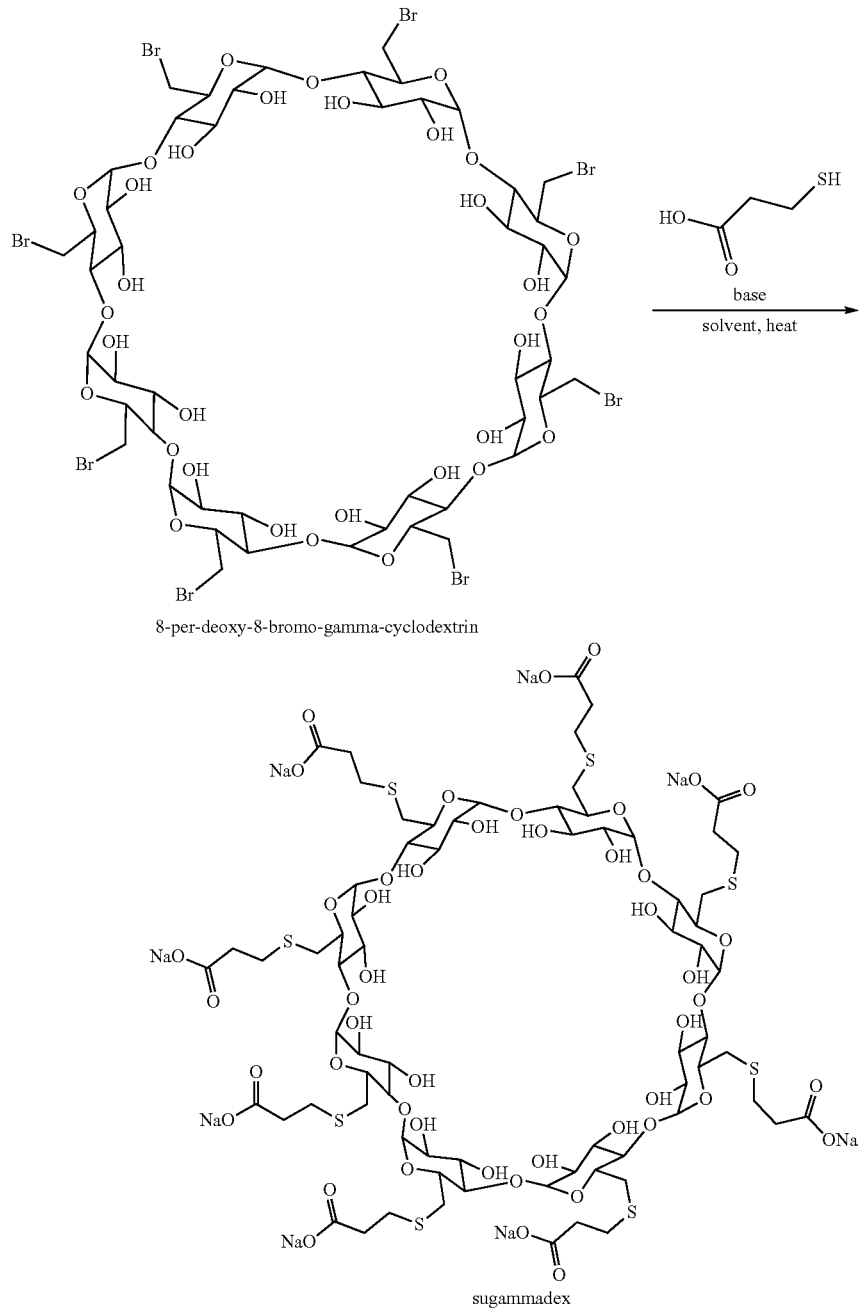

8-per-deoxy-8-bromo-gamma-cyclodextrin sugammadex

In a 30 L reactor, 8-per-deoxy-8-bromo-γ-cyclodextrin (1000.0 g, 493.8 mmol, 88.9 wt%) was dissolved in NMP (5 L) and 3-mercaptopropionic acid (721 mL, 8292 mmol) was added. The solution was cooled to 20° C. A sodium hydroxide-water solution (4 L, 16.06 mol, 13.8 wt%) was added to the solution in the 30 L reactor over 4 hours while maintaining the temperature between 18° C. to 23° C. After the addition was complete, the reaction mixture was heated to 50° C. and stirred for 3 h. The desired product was isolated. Isolation was achieved by adjusting the pH to from 8.5 to 9.5 using 6 N aqueous HCl (597 mL, 3.581 mol). Methanol (6 L) was then added at 18° C. to 20° C. over 4 h and the mixture was stirred for about 2 h at 18° C. to 20° C. The slurry was then filtered, and the solid was washed with 8:1 methanol:water (v/v) (5 L). The obtained solid was dried under vacuum to yield the desired sugammadex product in 1.041 kg (93.76 wt%, 91.4% isolated yield).

PREPARATION OF SUGAMMADEX FROM 8-PER-DEOXY-8-BROMO-GAMMA-CYCLODEXTRIN AND DISODIUM 3-MERCAPTOPROPIONATE

In another aspect, there is provided a process for the preparation of sugammadex

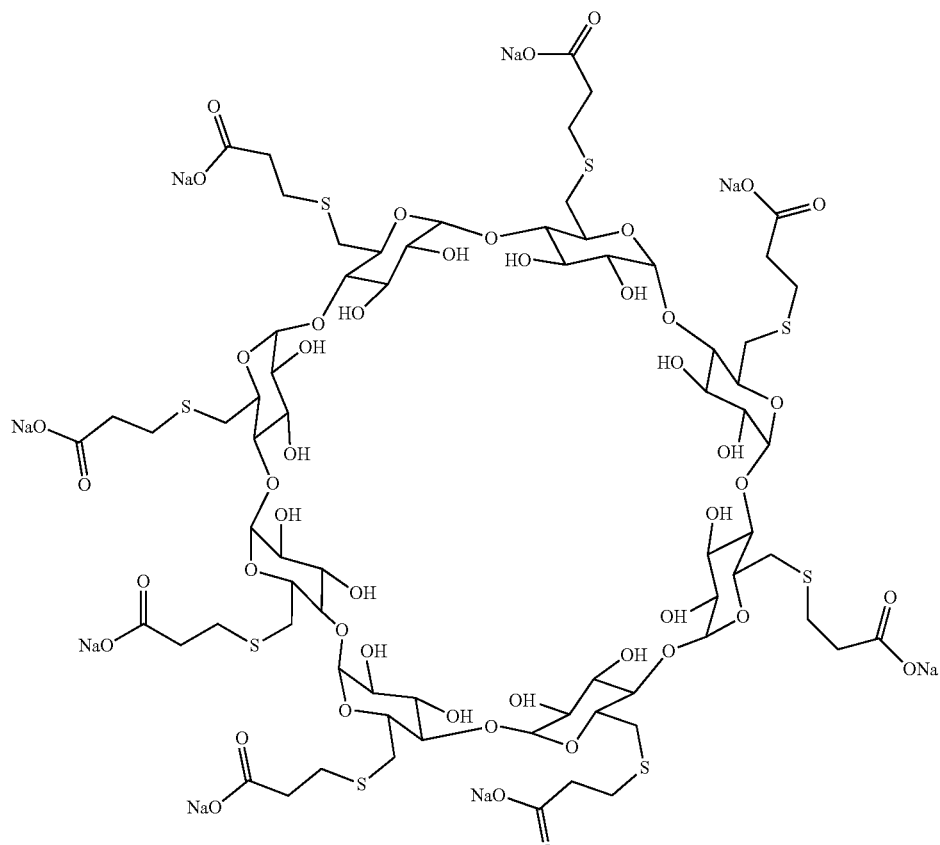

sugammadex comprising:
dissolving a solubility enhancing reagent in a solvent mixture to form a first solution;
adding disodium 3-mercaptopropionate to the first solution to form a second solution;
adding 8-per-deoxy-8-bromo-γ-cyclodextrin to the second solution to form a third solution;
stirring the third solution in the presence of heat; and
isolating the sugammadex product.

Solubility enhancing reagents suitable for use in the process are available commercially. In one embodiment, the solubility enhancing reagent is selected from sodium 4-tosylate, sodium 3-tosylate, sodium 2-tosylate, sodium 2,4-dimethylbenzene sulfonate, sodium 4-isopropylbenzene sulfonate, sodium 4-ethylbenzene sulfonate, sodium 3-ethylbenzene sulfonate, sodium 2-ethylbenzene sulfonate, sodium 4-bromobenzene sulfonate, sodium 3-bromobenzene sulfonate, sodium 2-bromobenzene sulfonate, sodium 4-chlorobenzene sulfonate, sodium 3-chlorobenzene sulfonate, sodium 2-chlorobenzene sulfonate, sodium 4-fluorobenzene sulfonate, sodium 3-fluorobenzene sulfonate, sodium 2-fluorobenzene sulfonate, sodium 4-methyoxybenzene sulfonate, sodium 3-methyoxybenzene sulfonate, sodium 2-methyoxybenzene sulfonate, sodium 1-hexanesulfonate, sodium 1-heptane sulfonate, N-lauroyl sarcosine, sodium dodecyl sulfate, sodium taurocholate, sodium benzene sulfonate, 3,5-dimethylbenzene sulfonate, 4-isopropylbenzenesulfonate and sodium benzoate. In a preferred embodiment, the solubility enhancing reagent is sodium 4-tosylate.

Suitable solvents useful for forming the first solution are available commercially. In one embodiment, the solvent is a mixture of water and an organic solvent. In another embodiment, the solvent is an organic solvent. In one embodiment, the organic solvent is selected from tetrahydrofuran (THF), 2-methyltetrahydrofuran (MeTHF), 1,2-dimethoxyethane (DME), dichloromethane (DCM), diethyl ether (Et$_2$O), anisole, cyclopentylmethyl ether (CPME), t-amyl alcohol, ethylene glycol diethyl ether, ethylene glycol dimethyl ether, or a mixture of two or more of any of the foregoing, optionally in further admixture with water. In a preferred embodiment, the solvent is a mixture of water and tetrahydrofuran (THF).

As noted above, the third solution is stirred in the presence of heat. In one embodiment, the solution is heated to a temperature between 20° C. and 100° C. In another embodiment, the solution is heated to a temperature between 40° C. and 60° C. In one embodiment, the solution is heated to a temperature of about 50° C. In one embodiment, the solution is stirred for at least 2 hours while the temperature is maintained in accordance with any of the foregoing temperatures. In another embodiment, the solution is stirred for from 2 to 30 hours while the temperature is maintained in accordance with any of the foregoing temperatures. In another embodiment, the solution is stirred for about 10 hours at about 50° C.

The sugammadex is isolated by precipitation with an antisolvent. Suitable antisolvents are available commercially. In one embodiment, the antisolvent is selected from methanol, ethanol, isopropanol, and tetrahydrofuran. In a preferred embodiment, the antisolvent is methanol. Preferably the antisolvent is added slowly. In one embodiment, the antisolvent is added over at least 20 minutes. In another embodiment, the antisolvent is added over a period of 20 minutes to 20 hours. In another embodiment, the antisolvent is added over about 50 minutes.

After the antisolvent according to any of the above described embodiments has been added, the resulting solution is optionally stirred to form a slurry. In one embodiment, the solution is stirred for at least 30 minutes. In another embodiment, the solution is stirred for from 30 minutes to 24 hours. In a preferred embodiment, the solution is stirred for about 16 hours after the addition of antisolvent.

The slurry formed is then filtered and washed with antisolvent or a mixture of water and antisolvent. The thus obtained solid may be dried, optionally under vacuum, to yield the isolated sugammadex product. In one embodiment, 1 volume of antisolvent according to any of the above embodiments is used to wash the solid. In a preferred embodiment, 3 volumes of an antisolvent/water mixture according to any of the above embodiments are used to wash the sugammadex solid.

Example 2: Preparation of Sugammadex From 8-per-deoxy-8-bromo-γ-cyclodextrin and Disodium 3-Mercaptopropionate

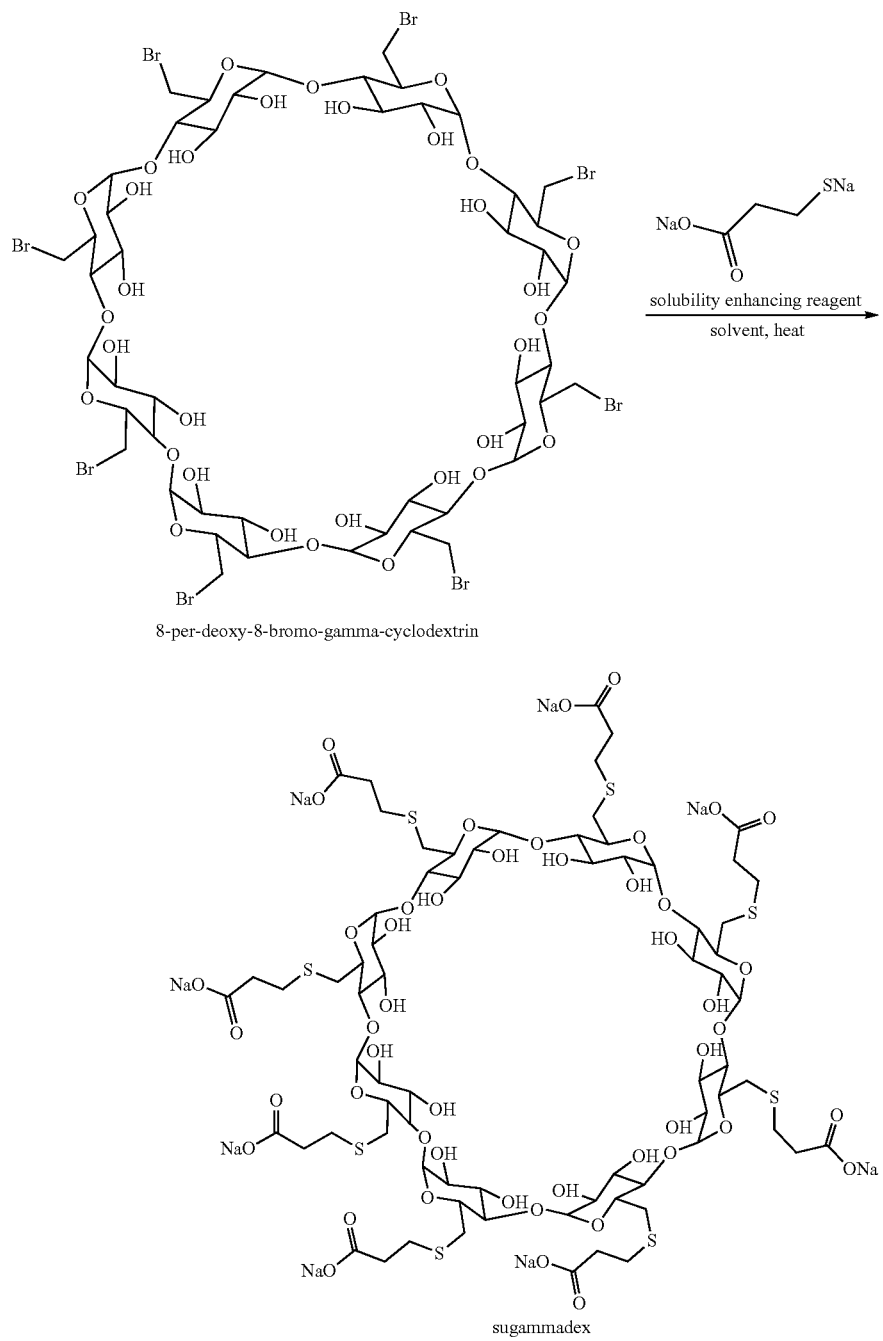

Sodium 4-tosylate (1.53 g, 7.50 mmol, 95 wt%) was dissolved in a mixture of THF (42.5 mL) and water (10 mL) to form a first solution. Disodium 3-mercaptopropionate (9.04 g, 37.5 mmol, 62 wt%) was charged into the first solution in two portions to form a second solution. 8-per-deoxy-8-bromo-γ-cyclodextrin (5.00 g, 2.50 mmol, 85 wt%) was charged into the second solution in five portions to form a third solution. The resulting solution was heated to 50° C. and maintained for 10 hours while stirring. The desired product was isolated. Isolation was achieved by adjusting the pH was adjusted to 7-14 using 18% aqueous HCl or 19% NaOH aqueous solution. Water (5 mL) was added after pH adjustment and an aqueous layer and an organic layer were formed. The aqueous layer was collected. Methanol (18 mL) was then added to the collected layer at 23° C., forming a precipitate. The slurry was stirred for 1 h at 23° C., then methanol (11 mL) was slowly charged to the slurry over 45 minutes. The slurry was filtered and the solid was washed with a mixture of methanol and water (15 mL, 8:1). The obtained solid was dried under vacuum to yield the desired sugammadex product. The analytical data characterizing the obtained sugammadex was in agreement with characterizations of the same provided in the literature. Adam, J. M., et al. J. Med. Chem. 2002, 45, 1806-1816.

PREPARATION OF
8-PER-DEOXY-8-BROMO-GAMMA-CYCLODEXTRIN FROM
GAMMA-CYCLODEXTRIN

In another aspect, there is provided a process for the preparation of 8-per-deoxy-8-bromo-γ-cyclodextrin of the formula:

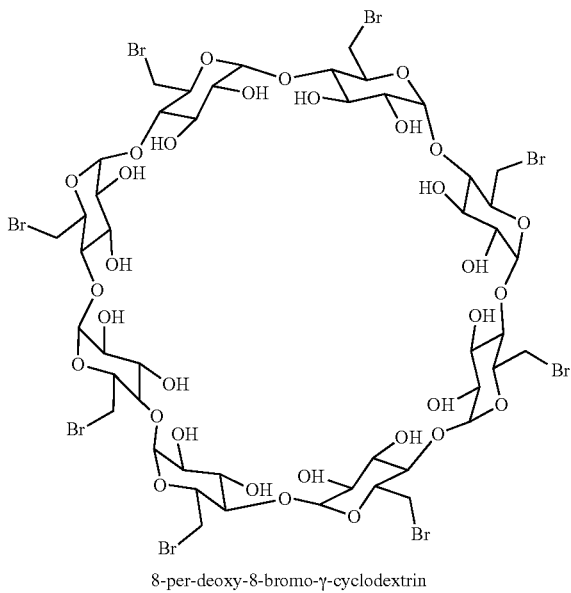 [SMILES: OC1C2OC(CBr)C(OC3OC(CBr)C(OC4OC(CBr)C(OC5OC(CBr)C(OC6OC(CBr)C(OC7OC(CBr)C(OC8OC(CBr)C(OC9OC(CBr)C(O2)C(O)C9O)C(O)C8O)C(O)C7O)C(O)C6O)C(O)C5O)C(O)C4O)C(O)C3O)C1O]

8-per-deoxy-8-bromo-γ-cyclodextrin comprising:
forming a solution comprising γ-cyclodextrin of the formula:

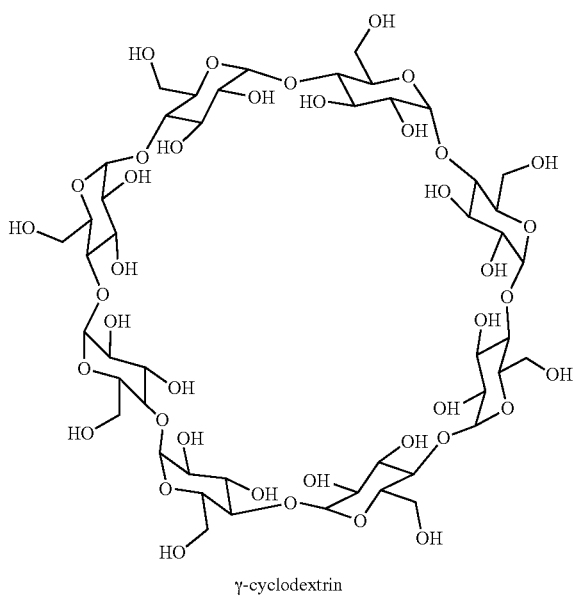 [SMILES: OCC1OC2OC3C(CO)OC(OC4C(CO)OC(OC5C(CO)OC(OC6C(CO)OC(OC7C(CO)OC(OC8C(CO)OC(OC9C(CO)OC(OC1C(O)C2O)C(O)C9O)C(O)C8O)C(O)C7O)C(O)C6O)C(O)C5O)C(O)C4O)C(O)C3O]

γ-cyclodextrin an organic solvent; and
a brominating agent;
heating the resulting solution; and
isolating the 8-per-deoxy-8-bromo-γ-cyclodextrin. In a preferred embodiment, an amount of water sufficient to quench the reaction is added to the resulting solution prior to isolation.

Suitable γ-cyclodextrin is commercially available. Typical commercially available γ-cyclodextrin comprises about 10% water by weight. Preferably the γ-cyclodextrin is anhydrous, comprising less than 10,000 ppm water by weight. More preferably, the γ-cyclodextrin comprises less than 1000 ppm water by weight. Suitably γ-cyclodextrin may be obtained from commercial sources and dried to the desired degree by methods known to those of ordinary skill in the art. Such methods include, but are not limited to, azeotropic distillation with a suitable organic solvent (such as DMF), or by drying over $P_2O_5$ at elevated temperatures (e.g., 100° C.) under vacuum. In one embodiment, the γ-cyclodextrin is dried through azeotropic distillation with DMF until the KF (Karl Fischer titration) value is less than 0.1%.

Suitable organic solvents are available commercially. In one embodiment, the organic solvent is N,N-dimethylformamide (DMF), N,N-diethylformamide (DEF), N,N-dibutylformamide, N,N-dimethylacetamide (DMA), 1-methyl-2-pyrrolidinone (NMP), 1-ethyl-2-pyrrolidone, 1-octyl-2-pyrrolidone, or 1-cyclohexyl-2-pyrrolidone, or mixtures thereof. In a preferred embodiment, the organic solvent is N,N-dimethylformamide (DMF). In another preferred embodiment, the γ-cyclodextrin is anhydrous and the organic solvent is N,N-dimethylformamide (DMF). As one skilled in the art will appreciate, the volume of γ-cyclodextrin and solvent solution may vary widely depending on quantity needed. Typically, and in one embodiment, the volume will range between 5 to 20V. In another embodiment, the volume is 12V.

Suitable brominating agents include, but are not limited to, N-(bromomethylene)-N-alkylmethanaminium bromides, which are available commercially or can be prepared from methods well known to those of ordinary skill in the art. See, e.g., Giles, P. R. and Marson, C. M. (2001). Dimethylbromomethyleneammonium Bromide. In Encyclopedia of Reagents for Organic Synthesis, (Ed.). doi:10.1002/047084289X.rd317m. Exemplary N-(bromomethylene)-N-alkylmethanaminium bromides include those of the structural formula:

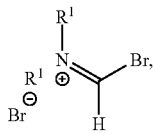

wherein each $R^1$ is independently ($C_1$-$C_6$) alkyl. In one embodiment, each $R^1$ is independently methyl (commercial), ethyl, n-propyl or n-butyl. In one embodiment, each $R^1$ is independently methyl, ethyl, or n-butyl. Suitable brominating agents also include, but are not limited to, bromomethylenemorpholinium bromide (alternatively referred to as N-(bromomethylene)-N-morpholinium bromide) having the structure:

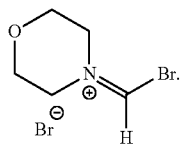

See, e.g., Chmurski, K.; Defaye, J.; Tetrahedron Letters 1997, 38, 7365-7368.

Thus, in one embodiment, the brominating agent is selected from N-(bromomethylene)-N-alkylmethanaminium bromide of the formula:

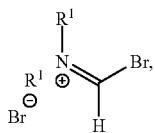

wherein each $R^1$ is independently methyl, ethyl, or n-butyl, and bromomethylenemorpholinium bromide (alternatively referred to as N-(bromomethylene)-N-morpholinium bromide) of the formula:

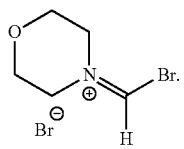

In a preferred embodiment, the brominating agent is N-(bromomethylene)-N-alkylmethanaminium bromide of the formula:

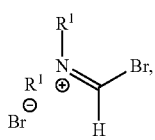

wherein each $R^1$ is methyl. In such embodiments, the N-(bromomethylene)-N-alkylmethanaminium bromide is referred to herein as N-(bromomethylene)-N-methylmethanaminium bromide.

As one skilled in the art will appreciate, the quantity of brominating agent used will vary in proportion to the quantity of γ-cyclodextrin to be brominated. For example, the amount of N-(bromomethylene)-N-alkylmethanaminium bromide will typically range from 12 to 24 equivalents with respect to the amount of γ-cyclodextrin. In a preferred embodiment, the amount of N-(bromomethylene)-N-alkylmethanaminium bromide is 20 equivalents with respect to the amount of γ-cyclodextrin.

The solution comprising the γ-cyclodextrin, organic solvent, and an N-(bromomethylene)-N-alkylmethanaminium bromide may be formed by any order of addition. Thus, in one embodiment, the γ-cyclodextrin is added to the organic solvent prior to the addition of the N-(bromomethylene)-N-alkylmethanaminium bromide. In another embodiment, the N-(bromomethylene)-N-alkylmethanaminium bromide is added to the organic solvent prior to the addition of the γ-cyclodextrin. In a preferred embodiment, anhydrous γ-cyclodextrin is added to the organic solvent and solid N-(bromomethylene)-N-alkylmethanaminium bromide is added portion-wise to the solution.

The resulting mixture is then heated at a temperature and for a time sufficient to replace each of the primary hydroxyl groups of the γ-cyclodextrin with bromine. Minimal and optimal time and temperatures for the bromination can be assessed by methods known to those of skill in the art, such as by measuring (e.g., by HPLC) the amount of 8-per-deoxy-8-bromo-γ-cyclodextrin produced by the described process at selected time points at each of a range of temperatures, then selecting the combination of time and reaction temperature that results in an acceptable (or desired) amount and rate of conversion. The amount of time required is generally inversely proportional to the temperature. In one embodiment, the mixture is heated to a temperature between 40° C. and 80° C. In another embodiment, the mixture is heated to a temperature of 70° C. In one embodiment, the reaction time is from 4 hours to 48 hours and the reaction temperature is maintained at from 40° C. to 80° C. In another embodiment the reaction time is 6 hours and the temperature is 70° C.

After the heated mixture is allowed to react at a suitable temperature and time in accordance with any of the embodiments described above, the reaction is quenched by mixing the resulting mixture with water prior to isolation of the 8-per-deoxy-8-bromo-γ-cyclodextrin. Amounts of water typically range from 10 to 500 equivalents (in some embodiments from 10 to 300 equivalents) with respect to the amount of γ-cyclodextrin. In one embodiment, the water is added while the temperature is maintained between 25° C. to 70° C. In another embodiment, the water is added while the temperature is maintained at 50° C. Upon the addition of the water solution, the mixture is then stirred for 1 hour to 24 hours (in another embodiment for 2 hours to 24 hours) at the selected temperature. In one non-limiting embodiment, the mixture is stirred for about 2 hours at about 50° C. The mixture is then optionally allowed to cool to room temperature prior to isolation.

The thus produced 8-per-deoxy-8-bromo-γ-cyclodextrin is then isolated. Isolation is achieved by precipitating the 8-per-deoxy-8-bromo-γ-cyclodextrin from the solution by the addition of an antisolvent, optionally followed by filtration and drying.

Suitable antisolvents include water, mixtures of water and methanol, water and ethanol, and water and ethers. Non-limiting examples of ethers include dialkyl ethers such as diethyl ether, 2-methoxy-2-methylpropan-1-ol, cyclic ethers such as tetrahydrofuran, 2-methyl tetrahydrofuran, and 1,4-dioxane, ethylene glycol derived ethers such as dimethyoxyethane, diethylene glycol methyl ether, diethylene glycol diethyl ether, and proglyme. The ratio of water:methanol, water:ethanol, and water:ether can each independently range from 1:99 to 99:1. Suitable, non-limiting amounts of antisolvent can range from 3 volumes to 20 volumes based on the amount of 8-per-deoxy-8-bromo-γ-cyclodextrin. In one embodiment, the solution is stirred as the antisolvent is added. In a preferred embodiment, the antisolvent is water.

In one embodiment, the temperature of the solution comprising the 8-per-deoxy-8-bromo-γ-cyclodextrin is maintained at (or cooled to) a first temperature range, optionally with the addition of antisolvent, to effect some amount of precipitation, then optionally further cooled to a second temperature range, optionally as additional antisolvent is added, to effect further precipitation of the 8-per-deoxy-8-bromo-γ-cyclodextrin. In another embodiment, the antisolvent is added over a time period of at least 30 minutes prior to cooling to the second temperature range. In one embodiment, the first temperature range is from 20° C. to 70° C. In another embodiment, the first temperature is from 30° C. to 70° C. In another embodiment, the first temperature is 40° C. In one embodiment, the second temperature range is from 0° C. to 40° C. In another embodiment, the second temperature is room temperature. In another embodiment, additional antisolvent according to any other of the above described embodiments is added as the temperature is cooled to the second temperature range. In one embodiment, the solution is allowed to age prior to filtration and drying. If further cooling to the second temperature is used, the solution is optionally allowed to age prior to further cooling. In each case, each comprising additional embodiments, the solution is allowed to age for at least one hour. In another embodiment, the solution is allowed to age from one hour to 24 hours prior. In a preferred embodiment, water is added at 40° C., then cooled to room temperature and aged for at least 1 hour.

The precipitated 8-per-deoxy-8-bromo-γ-cyclodextrin is optionally filtered and washed, optionally one, two, or more times, with antisolvent. As above, suitable antisolvents include water, mixtures of water and methanol, water and ethanol, and water and ethers. Non-limiting examples of ethers include dialkyl ethers such as diethyl ether, 2-methoxy-2-methylpropan-1-ol, cyclic ethers such as tetrahydrofuran, 2-methyl tetrahydrofuran, and 1,4-dioxane, ethylene glycol derived ethers such as dimethyoxyethane, diethylene glycol methyl ether, diethylene glycol diethyl ether, and proglyme. The ratio of water:methanol, water:ethanol, and water:ether can each independently range from 1:99 to 99:1. In a preferred embodiment, the precipitate is washed with water. The filtered precipitate is then optionally dried under vacuum prior to further use. As one skilled in the art will appreciate, the length of time required for drying will be inversely proportional to the temperature. Non-limiting examples of drying temperatures range from 20° C. to 60° C. (or from 25° C. to 50° C.), and non-limiting examples of drying time may range from about one hour to up to 5 or more days. The product 8-per-deoxy-8-bromo-γ-cyclodextrin from γ-cyclodextrin may be used as starting material in either of the above aspects of the invention for the production of sugammadex.

Example 3: Preparation of 8-per-deoxy-8-bromo-γ-cyclodextrin from γ-cyclodextrin Solid N-(bromomethylene)-N-methylmethanaminium bromide (35.2 g, 154 mmol) was added portionwise to a solution of anhydrous γ-cyclodextrin (10 g, 7.71 mmol) and DMF (120 mL) at 10° C. After the addition was complete, the solution was heated at 70° C. for 6 hours. The solution was then cooled to 50° C. and water (12.5 mL, 694 mmol,) was added and the solution was stirred at 50° C. for 2 h. The solution was allowed to cool to 40° C. and the product was precipitated by slowly adding water (80 mL). The resulting slurry was then cooled to room temperature and aged for at least one hour, allowing 8-per-deoxy-8-bromo-γ-cyclodextrin to precipitate. The precipitate was filtered and washed twice with water (60 mL). The solid 8-per-deoxy-8-bromo-γ-cyclodextrin from γ-cyclodextrin thus obtained was dried under vacuum at 50° C. to obtain the desired product (13.85 g). The analytical data characterizing the obtained 8-per-deoxy-8-bromo-γ-cyclodextrin product was in agreement with characterizations of the same provided in the literature. Gorin, B. I.; Riopelle, R. J.; Thatcher, G. R. J. Tetrahedron Lett. 1996, 37, 4647-4650.

Example 3A: Preparation of 8-per-deoxy-8-bromo-γ-cyclodextrin from γ-cyclodextrin Solid N-(bromomethylene)-N-methylmethanaminium bromide (3.18 kg, 14.65 mol) was added portionwise to a solution of anhydrous γ-cyclodextrin (1 kg, 0.77 mol) and DMF (16 L) at 0° C. After the addition was complete, the solution was heated at 70° C. for 6 hours. The solution was then cooled to 40° C. and water (1.4 L, 77 mmol) was added and the solution was stirred at 40° C. for 4 h. The product was precipitated by slowly adding water (12 L). The resulting slurry was then cooled to room temperature and aged for at least one hour, allowing 8-per-deoxy-8-bromo-γ-cyclodextrin to precipitate. The precipitate was filtered and washed three times with water (4 L). The solid 8-per-deoxy-8-bromo-γ-cyclodextrin from γ-cyclodextrin thus obtained was dried under vacuum at room temperature to obtain the desired product (1.44 kg). The analytical data characterizing the obtained 8-per-deoxy-8-bromo-γ-cyclodextrin product was in agreement with characterizations of the same provided in the literature. Gorin, B. I.; Riopelle, R. J.; Thatcher, G. R. J. Tetrahedron Lett. 1996, 37, 4647-4650.

PREPARATION OF 8-PER-DEOXY-8-BROMO-GAMMA-CYCLODEXTRIN FROM GAMMA-CYCLODEXTRIN

In another aspect, there is provided an alternative process for the preparation of 8-per-deoxy-8-bromo-γ-cyclodextrin of the formula:

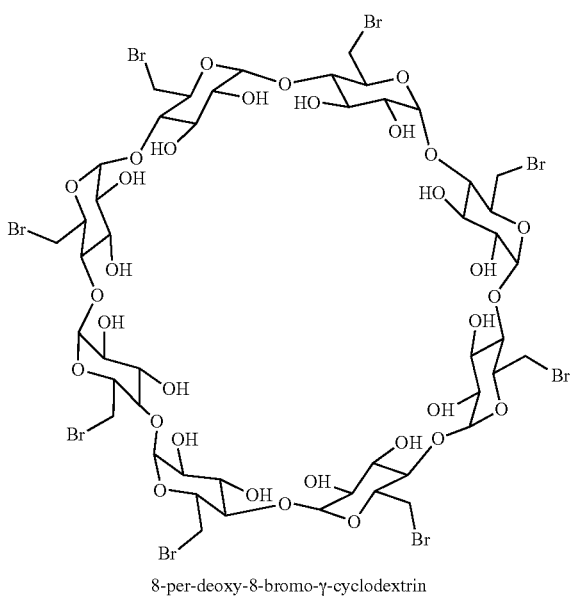 [SMILES: OC1C2OC(CBr)C(OC3OC(CBr)C(OC4OC(CBr)C(OC5OC(CBr)C(OC6OC(CBr)C(OC7OC(CBr)C(OC8OC(CBr)C(OC9OC(CBr)C(O2)C(O)C9O)C(O)C8O)C(O)C7O)C(O)C6O)C(O)C5O)C(O)C4O)C(O)C3O)C1O]

8-per-deoxy-8-bromo-γ-cyclodextrin comprising:
reacting γ-cyclodextrin of the formula:

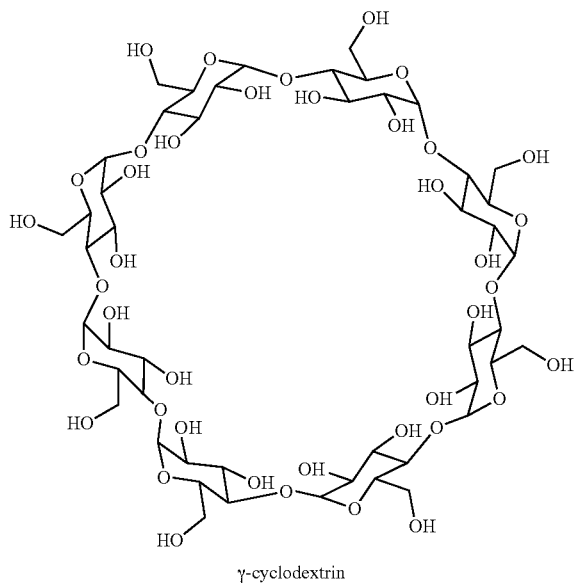 [SMILES: OCC1OC2OC3C(CO)OC(OC4C(CO)OC(OC5C(CO)OC(OC6C(CO)OC(OC7C(CO)OC(OC8C(CO)OC(OC9C(CO)OC(OC1C(O)C2O)C(O)C9O)C(O)C8O)C(O)C7O)C(O)C6O)C(O)C5O)C(O)C4O)C(O)C3O]

γ-cyclodextrin with an electrophilic brominating agent, a deoxygenating agent, and an acid in the presence of an organic solvent;
heating the resulting mixture;
adding to the mixture a solution comprising water and an acid and mixing the resulting solution; and
isolating the 8-per-deoxy-8-bromo-γ-cyclodextrin.

In a preferred embodiment, the electrophilic brominating agent is combined with the organic solvent, and the resulting solution is slowly added to a solution comprising the γ-cyclodextrin, the deoxygenating agent, acid, and the organic solvent. The resulting solution is then heated at a temperature of at least 30° C. for a time sufficient to fully brominate the primary hydroxyl groups of the γ-cyclodextrin with bromine.

Suitable γ-cyclodextrin is commercially available. Typical commercially available γ-cyclodextrin comprises about 10% water by weight. Preferably the γ-cyclodextrin used in the process is anhydrous, comprising less than 10,000 ppm water by weight. More preferably, the γ-cyclodextrin comprises less than 1000 ppm water by weight.

Suitable electrophilic brominating agents are commercially available. In one embodiment, the electrophilic brominating agent is 1,3-dibromo-5,5-dimethylhydantoin, N-bromoacetamide, N-bromosuccinimide, N-bromophthalimide, N-bromosaccharin, dibromoisocyanuric acid, monosodium bromoisocyanurate hydrate, bromodimethylsulfonium bromide, 5,5-dibromomeldrum's acid, 2,4,4,6-tetrabromo-2,5-cyclohexadienone, or bis(2,4,6-trimethylpyridine)-bromonium hexafluorophosphate. In a preferred embodiment, the electrophilic brominating agent is 1,3-dibromo-5,5-dimethylhydantoin.

The amount of electrophilic brominating agent, deoxygenating agent, acid, and solvent used will vary in proportion to the quantity of γ-cyclodextrin to be brominated. The amount of electrophilic brominating agent, which may be selected from any of those recited above, will typically range from 6 to 16 equivalents of γ-cyclodextrin. In one embodiment, the amount of electrophilic brominating agent is 10 equivalents. In another embodiment, the electrophilic brominating agent is 1,3-dibromo-5,5-dimethylhydantoin and the amount ranges from 6 to 16 equivalents. In another embodiment, the electrophilic brominating agent is 10.5 equivalents of 1,3-dibromo-5,5-dimethylhydantoin.

Suitable deoxygenating agents are available commercially. In one embodiment, the deoxygenating agent is an optionally substituted monophenyl, diphenyl and triphenyl compound selected from:

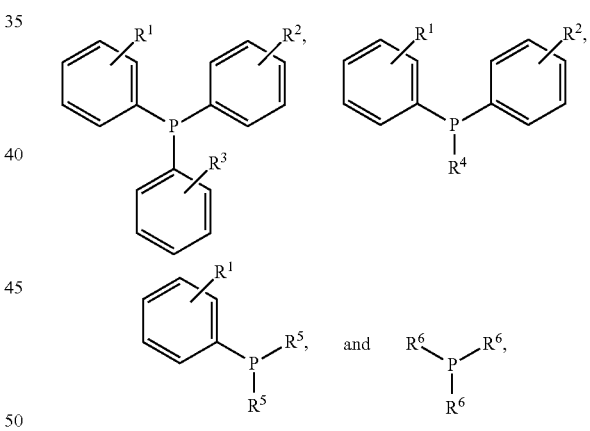

wherein each of $R^1$, $R^2$, and $R^3$ is independently selected from H, F, Cl, $CH_3$, $OCH_3$, and $CF_3$; $R^4$ is selected from methyl, ethyl, and benzyl; each $R^5$ is independently selected from methyl and ethyl; and each $R^6$ is independently selected from methyl, ethyl, n-butyl, and O-phenyl. In one embodiment, the deoxygenating agent is methyldiphenylphosphine.

The amount of deoxygenating agent used, which may be selected from any of those recited above, typically ranges from 12 to 32 equivalents (of γ-cyclodextrin). In one embodiment, the amount of deoxygenating agent is 20 equivalents. In another embodiment, the deoxygenating agent is methyldiphenylphosphine in an amount ranging from 12 to 32 equivalents. In another embodiment, the deoxygenating agent is 20 equivalents of methyldiphenylphosphine.

Suitable organic solvents are available commercially. In one embodiment, the organic solvent is N,N-dimethylformamide (DMF), N,N-diethylformamide (DEF), N,N-dibutylformamide, N,N-dimethylacetamide (DMA), N,N-diethylacetamide, 1-methyl-2-pyrrolidinone (NMP), 1-ethyl-2-pyrrolidone, 1-butyl-2-pyrrolidone, 1-octyl-2-pyrrolidone, 1-cyclohexyl-2-pyrrolidone, 1,3-dimethyl-2-imidazolidinone (DMI), or 1,3-dimethyl-3,4,5,6-tetrahydro-2(1H)-pyrimidinone (DMPU), or a mixture of any of the foregoing. In a preferred embodiment, the organic solvent is N,N-dimethylformamide (DMF).

After the electrophilic brominating agent, deoxygenating agent, acid and organic solvent are combined as described above, the mixture is allowed to react for a time sufficient to brominate each of the primary OH groups of the γ-cyclodextrin. Minimal and optimal time and temperatures for the bromination can be assessed by methods known to those of skill in the art, such as by measuring (e.g., by HPLC) the amount of 8-per-deoxy-8-bromo-γ-cyclodextrin produced by the described process at selected time points at each of a range of temperatures, then selecting the combination of time and reaction temperature that results in acceptable (or desired) amount and rate of conversion. The amount of time required is generally inversely proportional to the temperature. Minimally, the mixture is heated to at least about 30° C. In one embodiment, the mixture is heated to a temperature between 30 and 80° C. In another embodiment, the mixture is heated to a temperature between 50 and 70° C. In one embodiment, the reaction time is from 4 to 48 hours and the reaction temperature is maintained at from 30 to 80° C. In another embodiment the reaction time is from 4 to 12 hours and the temperature is from 50 to 70° C.

In some embodiments, where certain combinations of electrophilic bromination reagent, deoxygenating agent and solvent are used, it might be advantageous to use an acid. In such embodiments, suitable acids include organic and inorganic acids. Non-limiting examples of such acids are commercially available and include, for example: methanesulfonic acid, p-toluenesulfonic acid, trifluoroacetic acid, trifluoromethanesulfonic acid, acetic acid, sulfuric acid, phosphoric acid, and hydrobromic acid. In a preferred embodiment, the acid is methanesulfonic acid. The amount of such acid used, which may be selected from any of those recited above, typically ranges from 0.1 mol% (0.001 equivalents) to 10 equivalents of γ-cyclodextrin. In one embodiment, the acid is selected from any of those recited above and the amount of acid used is 2 mol% (0.02 equivalents). In one embodiment, the acid is methanesulfonic acid and the amount used is 2 mol%.

After the heated mixture is allowed to react at a suitable temperature and time in accordance with any of the embodiments described above, the reaction is quenched by mixing the resulting mixture with a solution comprising water and an acid. Optionally, additional water is added following the addition of the solution comprising water and the acid. Suitable acids are commercially available. Non limiting examples of such acids include hydrobromic acid, trifluoroacetic acid, and trifluoromethane sulfonic acid. In one embodiment, the acid is aqueous hydrobromic acid (e.g., 48% aqueous hydrobromic acid). Amounts of such aqueous acid solution typically range from 6 to 20 equivalents, preferably 10 equivalents with regard to the amount of γ-cyclodextrin. In one embodiment, the water-acid solution is added while the temperature is maintained at from 25 ° C. to 70 ° C. In another embodiment, the temperature is increased to 60° C. Upon the addition of the water-acid solution, the mixture is then stirred for 2 to 24 hours at the selected temperature. In one non-limiting embodiment, the mixture is stirred for about 6 hours at about 60° C. The mixture is then optionally allowed to cool to room temperature prior to isolation.

Isolation of the 8-per-deoxy-8-bromo-γ-cyclodextrin may be achieved by precipitation. Precipitation may be achieved by the slow addition of antisolvent. As above, suitable antisolvents include water, mixtures of water and methanol, water and ethanol, and water and ethers. Non-limiting examples of ethers include dialkyl ethers such as diethyl ether, 2-methoxy-2-methylpropan-1-ol, cyclic ethers such as tetrahydrofuran, 2-methyl tetrahydrofuran, and 1,4-dioxane, ethylene glycol derived ethers such as dimethyoxyethane, diethylene glycol methyl ether, diethylene glycol diethyl ether, and proglyme. The ratio of water:methanol, water:ethanol, and water:ether can each independently range from 1:99 to 99:1. In one embodiment, the antisolvent is a 1:9 (v:v) methanol:water mixture. The resulting slurry is optionally aged for at least 1 hour, up to 24 hours. The thus precipitated 8-per-deoxy-8-bromo-γ-cyclodextrin is optionally washed once or twice with antisolvent. In one embodiment, the antisolvent comprises a solution of water and methanol.

The precipitated 8-per-deoxy-8-bromo-γ-cyclodextrin is optionally filtered and washed, optionally one, two or more times with an antisolvent. As above, suitable antisolvents include water, mixtures of water and methanol, water and ethanol, and water and ethers. Non-limiting examples of ethers include dialkyl ethers such as diethyl ether, 2-methoxy-2-methylpropan-1-ol, cyclic ethers such as tetrahydrofuran, 2-methyl tetrahydrofuran, and 1,4-dioxane, ethylene glycol derived ethers such as dimethyoxyethane, diethylene glycol methyl ether, diethylene glycol diethyl ether, and proglyme. The ratio of water:methanol, water:ethanol, and water:ether can each independently range from 1:99 to 99:1. In a preferred embodiment, the precipitate is washed with methanol:water and then methanol. The filtered precipitate is then optionally dried under vacuum prior to further use. As one skilled in the art will appreciate, the length of time required for drying will be inversely proportional to the temperature. Non-limiting examples of drying temperatures range from 20° C. to 60° C. (or from 25° C. to 50° C.), and non-limiting examples of drying time may range from about one hour to up to 5 or more days. The product 8-per-deoxy-8-bromo-γ-cyclodextrin from γ-cyclodextrin may be used as starting material in either of the above aspects of the invention for the production of sugammadex.

Example 4: Preparation of 8-per-deoxy-8-bromo-γ-cyclodextrin from γ-cyclodextrin

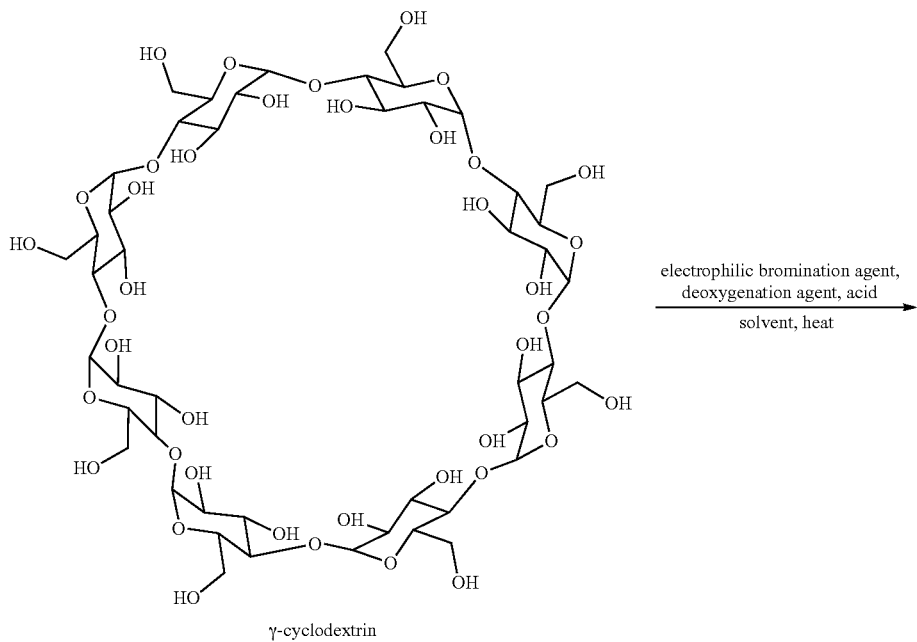

γ-cyclodextrin

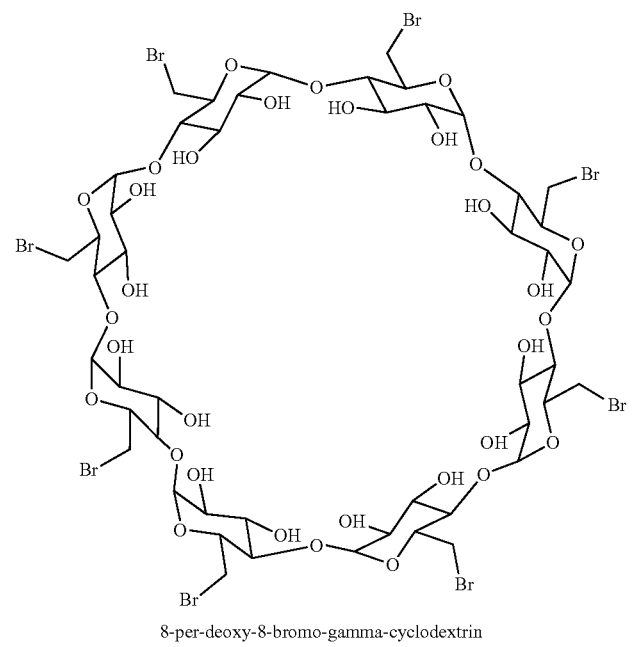

8-per-deoxy-8-bromo-gamma-cyclodextrin

A solution of 1,3-dibromo-5,5-dimethylimidazolidine-2,4-dione (24.0 g, 84.0 mmol) in DMF (23.4 ml) was slowly added to a solution of anhydrous γ-cyclodextrin (10.4 g, 8.0 mmol), methyldiphenylphosphine (29.8 mL, 160 mmol) in DMF (105 mL) at 0° C. After the addition was complete, the mixture was heated at 55° C. for 9 h.

The mixture was then heated to 60° C. 48% hydrobromic acid in water (9 mL, 80 mmol) and water (15 mL, 1.5 volumes) were added sequentially. The resulting mixture was then stirred at 60° C. for 6 h, then cooled to room temperature. The product was precipitated by the slow addition of a 1/9 (v/v) methanol/water mixture (228 mL). The slurry was aged for at least 1 h; the precipitate was filtered then washed twice with water:methanol 1/1 (v/v) (40 mL) and twice with methanol (30 mL). The solid was then dried under vacuum at 50° C. to obtain the desired product (14.8 g). The analytical data characterizing the obtained 8-per-deoxy-8-bromo-γ-cyclodextrin product was in agreement with characterizations of the same provided in the literature. Gorin, B. I.; Riopelle, R. J.; Thatcher, G. R. J. Tetrahedron Lett. 1996, 37, 4647-4650.

We claim:

1. A process for the preparation of a sugammadex:

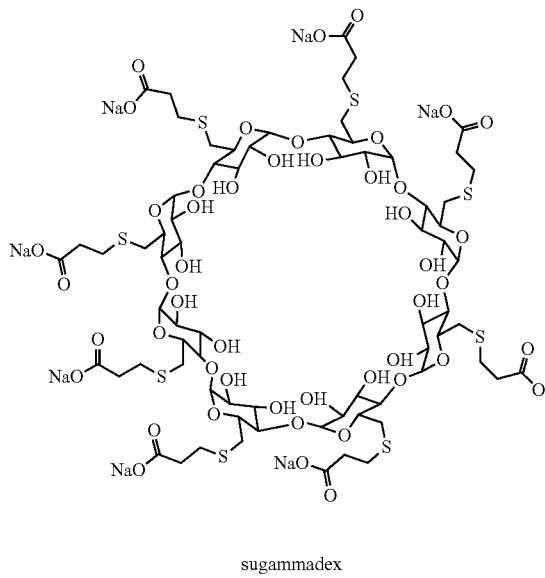

sugammadex comprising:

reacting γ-cyclodextrin of the formula:

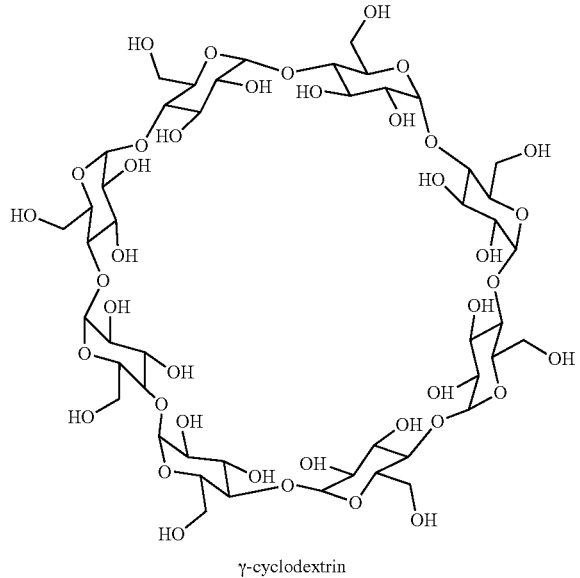 [SMILES: OCC1OC2OC3C(CO)OC(OC4C(CO)OC(OC5C(CO)OC(OC6C(CO)OC(OC7C(CO)OC(OC8C(CO)OC(OC9C(CO)OC(OC1C(O)C2O)C(O)C9O)C(O)C8O)C(O)C7O)C(O)C6O)C(O)C5O)C(O)C4O)C(O)C3O]

γ-cyclodextrin with an electrophilic brominating agent to brominate γ-cyclodextrin, a deoxygenating agent, and an acid in the presence of an organic solvent;

heating the resulting mixture;

adding to the mixture a solution comprising water and an acid and mixing the resulting solution to produce the 8-per-deoxy-8-bromo-γ-cyclodextrin of the formula:

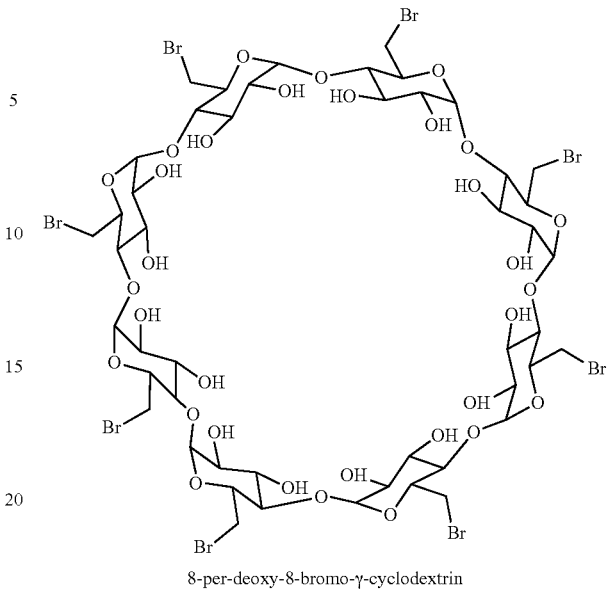

8-per-deoxy-8-bromo-γ-cyclodextrin dissolving 8-per-deoxy-8-bromo-γ-cyclodextrin in 1-methyl-2-pyrrolidinone;

adding 3-mercaptopropionic acid to form a first solution;

dissolving a base in water to form a base-water solution;

adding the base-water solution to the first solution at a rate sufficient to maintain the temperature of the resulting solution between about 5° C. and 40° C., wherein the base in the base-water solution is selected sodium hydroxide, sodium carbonate, and sodium phosphate;

stirring the resulting solution in the presence of heat;

adjusting the pH of the resulting mixture to from 7 to 13; and isolating the sugammadex product.

2. The process of claim 1, wherein the concentration of base in the base-water solution ranges from 6% to 24%.

3. The process of claim 2, wherein the concentration of base in the base-water solution ranges from 13% to 14%.

4. The process of claim 2, wherein the base-water solution is added to the first solution over at least 1 hour.

5. The process of claim 3, wherein the resulting solution is heated to a temperature between 20 and 100° C. and then stirred for from 2 h to 30 hours.

6. The process of claim 1, wherein the sugammadex is isolated by the addition of antisolvent or a mixture of antisolvent and water.

7. The process of claim 1, wherein the γ-cyclodextrin has been dried through azeotropic distillation with DMF until the Karl Fischer titration value is less than 0.1%.

8. The process of claim 1, wherein the electrophilic brominating agent is combined with the organic solvent, and the resulting solution is added to a solution comprising the γ-cyclodextrin, the deoxygenating agent, acid, and the organic solvent.

9. The process of claim 8, wherein the electrophilic brominating agent is 1,3-dibromo-5,5-dimethylhydantoin, N-bromoacetamide, N-bromosuccinimide, N-bromophthalimide, N-bromosaccharin, dibromoisocyanuric acid, monosodium bromoisocyanurate hydrate, bromodimethylsulfonium, bromide, 5,5-dibromomeldrum's acid, 2,4,4,6-tetrabromo-2,5-cyclohexadienone, bis(2,4,6-trimethylpyridine)-bromonium hexafluorophosphate or N-(bromomethylene)-N-methylmethanaminium.

10. The process of claim 9, wherein the electrophilic brominating agent is 1,3-dibromo-5,5-dimethylhydantoin.

11. The process of claim 8, wherein the deoxygenating agent is an optionally substituted monophenyl, diphenyl and triphenyl compound selected from:

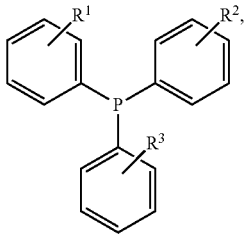

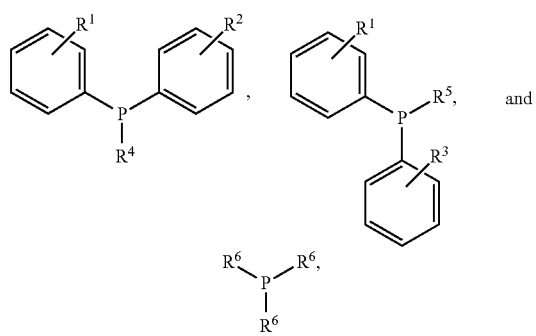

and wherein each of $R^1$, $R^2$, and $R^3$ is independently selected from H, F, Cl, $CH_3$, $OCH_3$, and $CF_3$;

$R^4$ is selected from methyl, ethyl, and benzyl;

each $R^5$ is independently selected from methyl and ethyl; and each $R^6$ is independently selected from methyl, ethyl, n-butyl, and O-phenyl.

12. The process of claim 11, wherein the deoxygenating agent is methyldiphenylphosphine.

13. The process of claim 8, wherein the acid is selected from methanesulfonic acid, p-toluenesulfonic acid, trifluoroacetic acid, trifluoromethanesulfonic acid, acetic acid, sulfuric acid, phosphoric acid, and hydrobromic acid.

14. The process of claim 8, wherein the organic solvent is N,N-dimethylformamide (DMF), N,N-diethylformamide (DEF), N,N-dibutylformamide, N,N-dimethylacetamide (DMA), N,N-diethylacetamide, 1-methyl-2-pyrrolidinone (NMP), 1-ethyl-2-pyrrolidone, 1-butyl-2-pyrrolidone, 1-octyl-2-pyrrolidone, 1-cyclohexyl-2-pyrrolidone, 1,3-dimethyl-2-imidazolidinone (DMI), or 1,3-dimethyl-3,4,5,6-tetrahydro-2(1H)-pyrimidinone (DMPU), or a mixture thereof.

15. The process of claim 8, wherein the solution is heated to at least about 25° C. and allowed to react from 4 to 48 hours, and then quenched by the addition of water and acid while stirring for 2 to 24 hours at a temperature from 25° C. to 70° C.

16. The process of claim 15, wherein the 8-per-deoxy-8-bromo-γ-cyclodextrin is isolated by precipitation with an antisolvent.

17. A process for the preparation of a sugammadex:

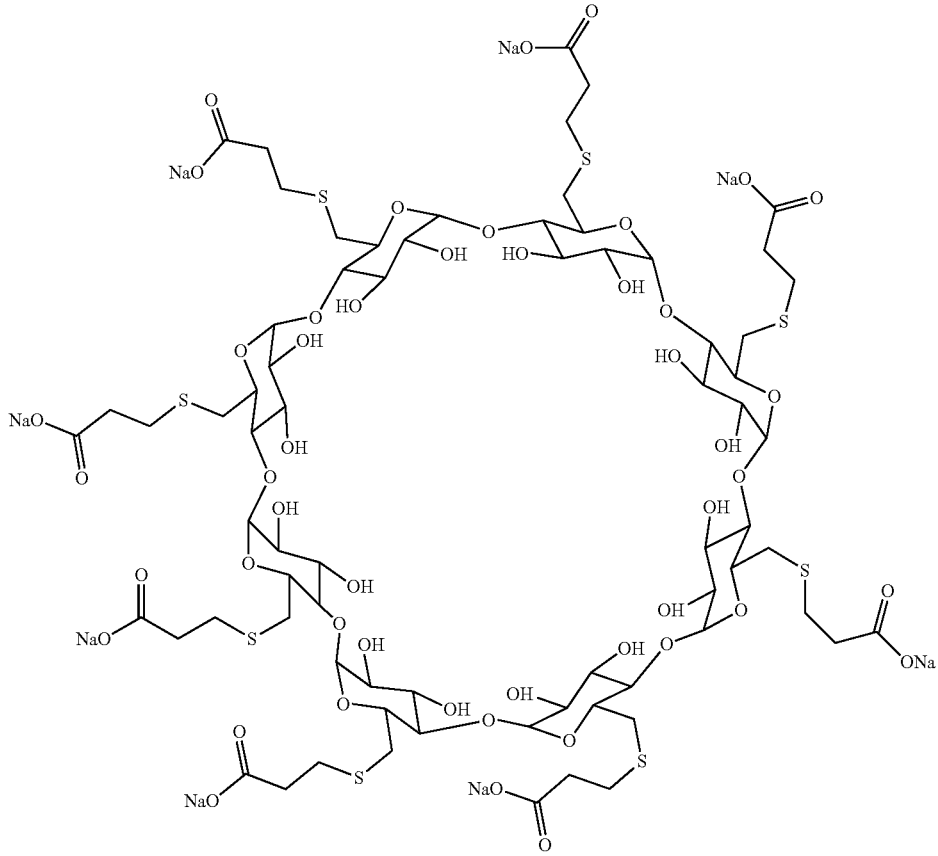

sugammadex comprising:

forming a solution comprising γ-cyclodextrin of the formula:

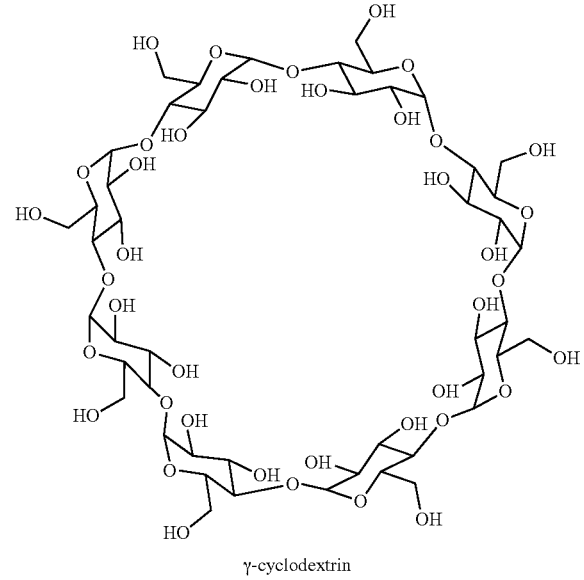 [SMILES: OCC1OC2OC3C(CO)OC(OC4C(CO)OC(OC5C(CO)OC(OC6C(CO)OC(OC7C(CO)OC(OC8C(CO)OC(OC9C(CO)OC(OC1C(O)C2O)C(O)C9O)C(O)C8O)C(O)C7O)C(O)C6O)C(O)C5O)C(O)C4O)C(O)C3O]

γ-cyclodextrin an organic solvent; and a brominating agent;

heating the resulting solution to brominate γ-cyclodextrin; wherein the mixture is heated to and maintained at a temperature between 40 and 80° C. and allowed to react from 4 hours to 48 hours and then quenched with water while maintaining the temperature between 25° C. to 70° C. to produce the 8-per-deoxy-8-bromo-γ-cyclodextrin of the formula:

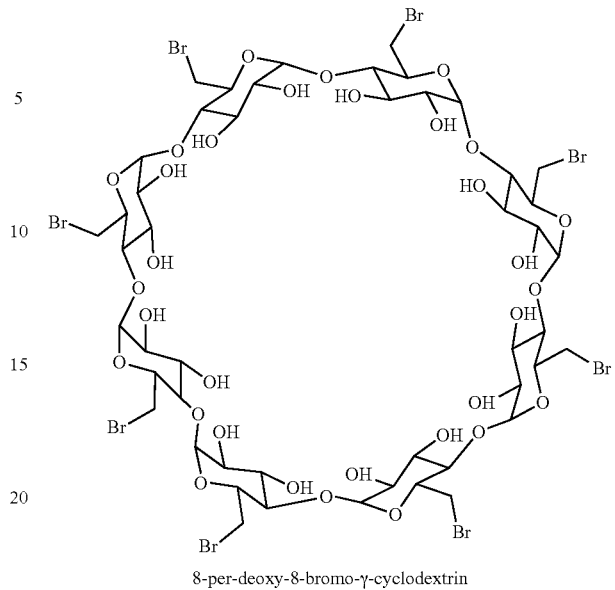

8-per-deoxy-8-bromo-γ-cyclodextrin dissolving 8-per-deoxy-8-bromo-γ-cyclodextrin in 1-methyl-2-pyrrolidinone;
adding 3-mercaptopropionic acid to form a first solution;
dissolving a base in water to form a base-water solution;
adding the base-water solution to the first solution at a rate sufficient to maintain the temperature of the resulting solution between about 5° C. and 40° C., wherein the base in the base-water solution is selected sodium hydroxide, sodium carbonate, and sodium phosphate;
stirring the resulting solution in the presence of heat;
adjusting the pH of the resulting mixture to from 7 to 13; and
isolating the sugammadex product.

18. The process of claim 17, wherein the γ-cyclodextrin is has been dried through azeotropic distillation with DMF until the Karl Fischer titration value is less than 0.1%.

19. The process of claim 18, wherein the organic solvent is N,N-dimethylformamide, N,N-diethylformamide, N,N-dibutylformamide, N,N-dimethylacetamide, 1-methyl-2-pyrrolidinone, 1-ethyl-2-pyrrolidone, 1-octyl-2-pyrrolidone, or 1-cyclohexyl-2-pyrrolidone, or mixtures thereof.

20. The process of claim 19, wherein the brominating agent is an N-(bromomethylene)-N-alkylmethanaminium bromide or a bromomethylenemorpholinium bromide.

21. The process of claim 17, wherein the 8-per-deoxy-8-bromo-γ-cyclodextrin is isolated by precipitation with an antisolvent.

* * * * *

UNITED STATES PATENT AND TRADEMARK OFFICE
CERTIFICATE OF CORRECTION

PATENT NO. : 11,634,511 B2  
APPLICATION NO. : 17/059925  
DATED : April 25, 2023  
INVENTOR(S) : Jamie M. McCabe Dunn et al.

Page 1 of 1

It is certified that error appears in the above-identified patent and that said Letters Patent is hereby corrected as shown below:

On the Title Page

Item (71) Applicant:  
Merck Sharp & Dohme Corp  
Jamie M. McCabe Dunn  
Nadine Kuhl  
Wenyong Chen  
Yang Cao  
Donald R. Gauthier, Jr.  
Alan Michael Hyde  
Susan L. Zultanski Should read:  
Merck Sharp & Dohme LLC Signed and Sealed this  
Twenty-seventh Day of May, 2025

Coke Morgan Stewart  
*Acting Director of the United States Patent and Trademark Office*